(12) United States Patent
Asiedu et al.

(10) Patent No.: US 12,073,559 B2
(45) Date of Patent: Aug. 27, 2024

(54) METHODS FOR AUTOMATED DETECTION OF CERVICAL PRE-CANCERS WITH A LOW-COST, POINT-OF-CARE, POCKET COLPOSCOPE

(71) Applicant: Duke University, Durham, NC (US)

(72) Inventors: Mercy Asiedu, Durham, NC (US); Nirmala Ramanujam, Durham, NC (US); Guillermo Sapiro, Durham, NC (US)

(73) Assignee: Duke University, Durham, NC (US)

( * ) Notice: Subject to any disclaimer, the term of this patent is extended or adjusted under 35 U.S.C. 154(b) by 702 days.

(21) Appl. No.: 17/282,093

(22) PCT Filed: Oct. 4, 2019

(86) PCT No.: PCT/US2019/054773
§ 371 (c)(1),
(2) Date: Apr. 1, 2021

(87) PCT Pub. No.: WO2020/076644
PCT Pub. Date: Apr. 16, 2020

(65) Prior Publication Data
US 2021/0374953 A1     Dec. 2, 2021

(51) Int. Cl.
*G06T 7/136* (2017.01)
*A61B 1/00* (2006.01)
(Continued)

(52) U.S. Cl.
CPC ...... *G06T 7/0012* (2013.01); *A61B 1/000094* (2022.02); *G06T 7/11* (2017.01);
(Continued)

(58) Field of Classification Search
CPC . A61B 1/000094; A61B 1/303; A61B 5/4331; A61B 5/7264; G06T 2207/10024;
(Continued)

(56) References Cited

U.S. PATENT DOCUMENTS

| 471,647 A | 3/1892 | Magoris |
|---|---|---|
| 4,210,133 A | 7/1980 | Castaneda |

(Continued)

FOREIGN PATENT DOCUMENTS

| WO | 2009029254 A1 | 3/2009 |
|---|---|---|
| WO | 2015077684 A1 | 5/2015 |
| WO | 2017173178 A1 | 10/2017 |

OTHER PUBLICATIONS

Vasudha, "Cervix Cancer Classification using Colposcopy Images by Deep Learning Method," Mar. 2018, International Journal of Engineering Technology Science and Research IJETSR, vol. 5, Issue 3, Mar. 2018, pp. 426-431.*

(Continued)

*Primary Examiner* — Omar S Ismail
(74) *Attorney, Agent, or Firm* — Myers Bigel, P.A.

(57) ABSTRACT

A method for automated detection of cervical pre-cancer includes: providing at least one cervigram; pre-processing the at least one cervigram; extracting features from the at least one pre-processed cervigram; and classifying the at least one cervigram as negative or positive for cervical pre-cancer based on the extracted features.

30 Claims, 9 Drawing Sheets

(51) Int. Cl.
  *G06T 7/00* (2017.01)
  *G06T 7/11* (2017.01)
  *G06T 7/168* (2017.01)

(52) U.S. Cl.
  CPC .............. *G06T 7/136* (2017.01); *G06T 7/168* (2017.01); *G06T 2207/20024* (2013.01); *G06T 2207/20081* (2013.01); *G06T 2207/20084* (2013.01); *G06T 2207/20132* (2013.01); *G06T 2207/30096* (2013.01)

(58) Field of Classification Search
  CPC . G06T 2207/10056; G06T 2207/20024; G06T 2207/20064; G06T 2207/20081; G06T 2207/20084; G06T 2207/20132; G06T 2207/30096; G06T 7/0012; G06T 7/11; G06T 7/136; G06T 7/168
  See application file for complete search history.

(56) References Cited

U.S. PATENT DOCUMENTS

| | | | |
|---|---|---|---|
| 5,259,836 A | 11/1993 | Thurmond et al. | |
| 5,406,938 A | 4/1995 | Mersch et al. | |
| 6,010,450 A | 1/2000 | Perkins | |
| 6,277,067 B1 | 8/2001 | Blair | |
| 6,447,444 B1 | 9/2002 | Avni et al. | |
| 6,463,438 B1* | 10/2002 | Veltri | G06V 20/695 706/15 |
| 6,496,718 B1 | 12/2002 | Lonky | |
| 6,526,980 B1 | 3/2003 | Tracy et al. | |
| 7,236,815 B2 | 6/2007 | Richards-Kortum et al. | |
| 7,664,300 B2 | 2/2010 | Lange et al. | |
| 8,503,747 B2 | 8/2013 | Park et al. | |
| 9,107,569 B2* | 8/2015 | Gupta | A61B 1/303 |
| 9,122,897 B2 | 9/2015 | Hernández-Cisneros | |
| 10,055,551 B2* | 8/2018 | Agaian | G06T 7/0012 |
| 2005/0049509 A1 | 3/2005 | Mansour et al. | |
| 2005/0080318 A1 | 4/2005 | Squicciarini | |
| 2005/0080412 A1 | 4/2005 | Ouchi | |
| 2005/0177027 A1 | 8/2005 | Hirata | |
| 2005/0277811 A1 | 12/2005 | Richards et al. | |
| 2006/0167340 A1 | 7/2006 | Pease et al. | |
| 2006/0204953 A1* | 9/2006 | Ptitsyn | G06T 7/0012 382/128 |
| 2007/0049764 A1 | 3/2007 | Ko et al. | |
| 2007/0135819 A1 | 6/2007 | Spiritos et al. | |
| 2007/0177009 A1 | 8/2007 | Bayer et al. | |
| 2007/0191678 A1 | 8/2007 | Sekiguchi | |
| 2007/0213590 A1 | 9/2007 | Squicciarini | |
| 2007/0232913 A1 | 10/2007 | Lau et al. | |
| 2008/0045791 A1 | 2/2008 | Gal et al. | |
| 2008/0058586 A1 | 3/2008 | Karpiel | |
| 2008/0058590 A1 | 3/2008 | Saadat et al. | |
| 2008/0058605 A1 | 3/2008 | Tyler | |
| 2008/0108869 A1 | 5/2008 | Sanders et al. | |
| 2008/0177142 A1 | 7/2008 | Roskopf | |
| 2009/0062662 A1 | 3/2009 | Zuluaga | |
| 2009/0062691 A1 | 3/2009 | Kim | |
| 2009/0076368 A1* | 3/2009 | Balas | A61B 1/042 600/407 |
| 2009/0082695 A1 | 3/2009 | Whitehead | |
| 2009/0203962 A1 | 8/2009 | Miller et al. | |
| 2009/0274349 A1* | 11/2009 | Cascio | G06T 7/0012 382/128 |
| 2010/0003704 A1* | 1/2010 | Cheng | C07K 16/084 435/7.21 |
| 2010/0030020 A1 | 2/2010 | Sanders et al. | |
| 2010/0033563 A1 | 2/2010 | Boehnlein et al. | |
| 2010/0061609 A1* | 3/2010 | Shinagawa | G06V 10/7715 382/131 |
| 2010/0217084 A1 | 8/2010 | Takakazu | |
| 2010/0024960 A1 | 9/2010 | Yu et al. | |
| 2010/0305503 A1 | 12/2010 | Fang et al. | |
| 2011/0002584 A1 | 1/2011 | Griffin | |
| 2011/0023885 A1 | 2/2011 | Vazales et al. | |
| 2011/0112435 A1 | 5/2011 | Ramanujam et al. | |
| 2011/0184243 A1 | 7/2011 | Wright et al. | |
| 2011/0188716 A1 | 8/2011 | Bennett et al. | |
| 2011/0190579 A1 | 8/2011 | Ziarno et al. | |
| 2011/0190580 A1 | 8/2011 | Bennett et al. | |
| 2011/0190581 A1 | 8/2011 | Bennett et al. | |
| 2011/0190582 A1* | 8/2011 | Bennett | A61B 1/00096 600/109 |
| 2011/0190595 A1 | 8/2011 | Bennett et al. | |
| 2011/0190596 A1 | 8/2011 | Hacker et al. | |
| 2011/0190689 A1 | 8/2011 | Bennett et al. | |
| 2011/0274338 A1* | 11/2011 | Park | G06T 7/0012 382/133 |
| 2012/0157767 A1* | 6/2012 | Jendoubi | G16H 30/20 600/109 |
| 2012/0172664 A1 | 7/2012 | Hayman et al. | |
| 2012/0253123 A1 | 10/2012 | Shimizu et al. | |
| 2013/0053657 A1 | 2/2013 | Ziarno et al. | |
| 2013/0066165 A1 | 3/2013 | Shemer et al. | |
| 2013/0137920 A1 | 5/2013 | Schaeffer et al. | |
| 2014/0005477 A1* | 1/2014 | Gupta | A61B 1/000094 600/109 |
| 2014/0088364 A1 | 3/2014 | Vail | |
| 2014/0243876 A1 | 8/2014 | Satoru | |
| 2015/0141742 A1 | 5/2015 | De et al. | |
| 2015/0150441 A1 | 6/2015 | Ouyang et al. | |
| 2016/0183778 A1 | 6/2016 | Nadershahi et al. | |
| 2016/0227994 A1 | 8/2016 | Gotsch et al. | |
| 2016/0262604 A1 | 9/2016 | Greenstein et al. | |
| 2016/0287063 A1* | 10/2016 | Ramanujam | A61B 1/00087 |
| 2016/0367148 A1* | 12/2016 | Froloff | A61B 1/0005 |
| 2017/0049312 A1 | 2/2017 | Seth et al. | |
| 2017/0064162 A1 | 3/2017 | Haraguchi et al. | |
| 2017/0245885 A1 | 8/2017 | Lenker | |
| 2017/0280988 A1 | 10/2017 | Barbato et al. | |
| 2018/0140320 A1 | 5/2018 | Aikawa et al. | |
| 2018/0317746 A1 | 11/2018 | Lalli et al. | |
| 2019/0130228 A1* | 5/2019 | Fu | G06N 5/01 |
| 2019/0150725 A1 | 5/2019 | Ramanujam et al. | |
| 2020/0005931 A1* | 1/2020 | Madabhushi | A61B 5/4381 |
| 2021/0249118 A1* | 8/2021 | Papagiannakis | G06T 7/0012 |

OTHER PUBLICATIONS

Zhiyun Xue,"Comparative performance analysis of cervix ROI extraction and specular reflection removal algorithms for uterine cervix image analysis," Mar. 3, 2007,Proc. of SPIE vol. 6512Medical Imaging, 2007, San Diego, CA, United States,pp. 2-8.*
P.S.Rama Praba,"Comparing Different Classifiers for Automatic Lesion Detection in Cervix Based on Colour Histogram," Feb. 25, 2013, Journal of Computer Applications (JCA),ISSN: 0974-1925, vol. VI, Issue 1, 2013,pp. 15-17.*
Abhishek Das,"Elimination of Specular reflection and Identification of ROI: The First Step in Automated Detection of Cervical Cancer using Digital Colposcopy," Jul. 28, 2011, 2011 IEEE International Conference on Imaging Systems and Techniques,pp. 1-3.*
Hayit Greenspan ,"Automatic Detection of Anatomical Landmarks in Uterine Cervix Images",Feb. 25, 2009,IEEE Transactions on Medical Imaging, vol. 28, No. 3, Mar. 2009,pp. 454-467.*
Natalia A. Obukhova,"Automated Image Analysis in Multispectral System for Cervical Cancer Diagnostic," Oct. 19, 2017, 2017 20th Conference of Open Innovations Association (FRUCT),pp. 345-350.*
Kelwin Fernandes,"Automated Methods for the Decision Support of Cervical Cancer Screening Using Digital Colposcopies," Jul. 6, 2018, IEEEAccess, vol. 6, 2018, pp. 33910-33924.*
Yeshwanth Srinivasan,"A Unified Model-Based Image Analysis Framework for Automated Detection of Precancerous Lesions in Digitized Uterine Cervix Images," Feb. 19, 2009,IEEE Journal of Selected Topics in Signal Processing, vol. 3, No. 1, Feb. 2009,pp. 101-109.*
Mercy Nyamewaa Asiedu,"Image processing and machine learning techniques to automate diagnosis of Lugol's iodine cervigrams for

(56) References Cited

OTHER PUBLICATIONS a low-cost point-ofcare digital colposcope," Feb. 13, 2018,Proceedings vol. 10485, Optics and Biophotonics in Low-Resource Settings IV; 1048508 (2018) https://doi.org/10.,pp. 1-9.*
International Search Report and Written Opinion for PCT/US2019/054773 mailed May 1, 2020, 11 pages.
"Anderson, R. Rox, and Parrish, John A., "The optics of human skin." Journal of Investigative Dermatology 77(1):13-19 (1981)."
"Cervical Cancer Prevention Initiatives at PATH Two decades of progress toward a world free of HPV-related cancers. LinkK http://screening.iarc.fr/doc/PATH_cxca_rep_to_world.pdf (2008)".
"Hasina, R., and Mark W. Lingen. "Angiogenesis in oral cancer." Journal of dental education 65(11): 1282-1290 (2001)".
"Liu, Quan, and Ramanujam, Nirmala "Sequential estimation of optical properties of a two-layered epithelial tissue model from depth-resolved ultraviolet-visible diffuse reflectance spectra." Applied Optics 45(19): 4776-4790 (2006)".
"Pittman, Roland N., and Brian R. Duling. "A new method for the measurement of percent oxyhemoglobin." Journal of Applied Physiology 38(2): 315-320 (1975)".
"Worcester, Sharon, "Novel device aims to make cervical cancer screening more accessible," MDedge:ObGyn, Aug. 2, 2017, 6 pages."
Adams, E. Kathleen, , et al., ""Impact of the National Breast and Cervical Cancer Early Detection Program on mammography and Pap test utilization among white, Hispanic, and African American women: 1996-2000." Cancer 109.S2: 348-358 (2007)".
Arifler, Dizem, , et al., ""Reflectance spectroscopy for diagnosis of epithelial precancer: model-based analysis of fiber-optic probe designs to resolve spectral information from epithelium and stroma." Applied Optics 44(20): 4291-4305 (2005)".
Arifler, Dizem, , et al., ""Spatially resolved reflectance spectroscopy for diagnosis of cervical precancer: Monte Carlo modeling and comparison to clinical measurements." Journal of Biomedical Optics 11(6): 064027-064027 (2006)."
Bender, Janelle E., , et al., ""A robust Monte Carlo model for the extraction of biological absorption and scattering in vivo." Biomedical Engineering, IEEE Transactions on 56(4): 960-968 (2009)".
Beumer, H.W, , et al., ""Detection of squamous cell carcinoma and corresponding biomarkers using optical spectroscopy." Otolaryngology-Head and Neck Surgery 144(3): 390-394 (2011)".
Brizel, David M., , et al., ""Tumor hypoxia adversely affects the prognosis of carcinoma of the head and neck." International Journal of Radiation Oncology* Biology* Physics 38(2): 285-289 (1997)".
Brown, J. Quincy, , et al., ""Quantitative optical spectroscopy: a robust tool for direct measurement of breast cancer vascular oxygenation and total hemoglobin content in vivo." Cancer Research 69(7): 2919-2926. (2009)".
Cardena-Turanzas, Marylou , et al., ""The clinical effectiveness of optical spectroscopy for the in vivo diagnosis of cervical intraepithelial neoplasia: where are we?." Gynecologic Oncology 107(1): S138-S146 (2007)."
Chang, Sung K., , et al., ""Combined reflectance and fluorescence spectroscopy for in vivo detection of cervical pre-cancer." Journal of Biomedical Optics 10(2): 024031.1-0240311.1 (2005)".
Chang, Vivide Tuan-Chyan, , et al., ""Quantitative physiology of the precancerous cervix in vivo through optical spectroscopy." Neoplasia 11(4): 325-332 (2009)".
Chang, Vivide Tuan-Chyan, , et al., ""Visible light optical spectroscopy is sensitive to neovascularization in the dysplastic cervix." Journal of Biomedical Optics 15(5): 057006-057006 (2010)."
Cuccia, David J., , et al., ""Quantitation and mapping of tissue optical properties using modulated imaging." Journal of Biomedical Optics 14(2): 024012-1-024012-133 (2009)".
De Veld, Diana CG, , et al., ""Autofluorescence and diffuse reflectance spectroscopy for oral oncology." Lasers in surgery and medicine 36.5 : 356-364 (2005)".
Delong, Elizabeth R., et al., "Comparing the Areas under Two or More Correlated Receiver Operating Characteristic Curves: A Nonparametric Approach", Biometrics 44(3), 1998, 837-845.

Dhar, Sulochana, , et al., ""A diffuse reflectance spectral imaging system for tumor margin assessment using custom annular photodiode arrays." Biomedical Optics express 3.12: 3211-3222(2012)".
Dubray, Bernard, , et al., ""Anemia is associated with lower local-regional control and survival after radiation therapy for head and neck cancer: a prospective study." Radiology 201(2) : 553-558 (1996)".
Ellsworth, Mary L., , et al., ""Measurement of hemoglobin oxygen saturation in capillaries." American Journal of Physiology-Heart and Circulatory Physiology 252(5): H1031-H1040 (1987)".
Follen, Michele, , et al., ""Optical technologies for cervical neoplasia: update of an NCI program project grant." Clinical Advances in Hematology and Oncology 3(1):41-53 (2005)".
Freeberg, J. A, , et al., ""The performance of fluorescence and reflectance spectroscopy for the in vivo diagnosis of cervical neoplasia; point probe versus multispectral approaches." Gynecologic Oncology 107(1): S248-S255(2007)".
Gao, Liang, , et al., ""Compact Image Slicing Spectrometer (ISS) for hyperspectral fluorescence microscopy." Optics express 17(15): 12293-12308 (2009)".
Georgakoudi, Irene, , et al., ""Trimodal spectroscopy for the detection and characterization of cervical precancers in vivo." American journal of obstetrics and gynecology 186(3): 374-382 (2002)".
Goldie, Sue J., , et al., ""Cost-effectiveness of cervical-cancer screening in five developing countries." New England Journal of Medicine 353(20): 2158-2168 (2005)".
Kujan, Omar, , et al., ""Screening programmes for the early detection and prevention of oral cancer." The Cochrane Library Issue 11(2010)".
Lane, Pierre M., , et al., ""Simple device for the direct visualization of oral-cavity tissue fluorescence." Journal of Biomedical Optics 11(2): 024006.1-024006.7 (2006)".
Lee, W. Robert, , et al., ""Anemia is associated with decreased survival and increased locoregional failure in patients with locally advanced head and neck carcinoma: a secondary analysis of RTOG 85-27." International Journal of Radiation Oncology* Biology* Physics 42(5 ): 1069-107".
Marin, Nena M., , et al., ""Diffuse reflectance patterns in cervical spectroscopy." Gynecologic Oncology 99(3): S116-S120 (2005)".
Marks, James S., , et al., ""Implementing recommendations for the early detection of breast and cervical cancer among low-income women." Morbidity and Mortality Weekly Report: Recommendations and Reports vol. 4 No. RR-2: 35-55 (2000)".
Mirabal, Yvette N., , et al., ""Reflectance spectroscopy for in vivo detection of cervical precancer." Journal of Biomedical Optics 7(4): 587-594 (2002)".
Mueller, JL , et al., "Portable Pocket colposcopy performs comparably to standard-of-care clinical colposcopy using acetic acid and Lugol's iodine as contrast mediators: an investigational study in Peru", BJOG, DOI: 10.1111/1471-0528.14326, Jul. 19, 2018, pp. 1321-1329.
Muller, Markus G., , et al., ""Spectroscopic detection and evaluation of morphologic and biochemical changes in early human oral carcinoma." Cancer 97(7): 1681-1692 (2003)".
Nordsmark, Marianne, , et al., ""Prognostic value of tumor oxygenation in 397 head and neck tumors after primary radiation therapy. An international multi-center study." Radiotherapy and Oncology 77(1): 18-24 (2005)".
Palmer, M.P. , et al., ""Monte Carlo-based inverse model for calculating tissue optical properties. Part 1: Theory and validation on synthetic phantoms," Appl. Opt. '15; 1062-1071 (2006)".
Pavlova, Ina, , et al., ""Fluorescence spectroscopy of oral tissue: Monte Carlo modeling with site-specific tissue properties." Journal of Biomedical Optics 14(1): 014009-014009 (2009)".
Phelps, Janelle E., , et al., ""Rapid ratiometric determination of hemoglobin concentration using UV-VIS diffuse reflectance at isosbestic wavelengths." Optics Express 18(18): 18779-18792 (2010)".
Rahman, Mohammed, , et al., ""Low-cost, multimodal, portable screening system for early detection of oral cancer." Journal of Biomedical Optics 13(3): 030502-030502 (2008)".
Sankaranarayanan, Rengasw , et al., ""Effect of screening on oral cancer mortality in Kerala, India: a cluster-randomised controlled trial." The Lancet 365(9475): 1927-1933 (2005".

(56) References Cited

OTHER PUBLICATIONS

Sankaranarayanan, Rengasw, et al., ""HPV screening for cervical cancer in rural India." New England Journal of Medicine 360(14): 1385-1394 (2009)".

Saslow, Debbie, , et al., ""American Cancer Society guideline for the early detection of cervical neoplasia and cancer." CA: a Cancer Journal for Clinicians 52(6) : 342-362.(2002)".

Schwarz, Richard A., , et al., ""Autofluorescence and diffuse reflectance spectroscopy of oral epithelial tissue using a depth-sensitive fiber-optic probe." Applied Optics 47(6) : 825-834 (2008)".

Sharwani, A., , et al., ""Assessment of oral premalignancy using elastic scattering spectroscopy." Oral Oncology 42.4: 343-349 (2006)".

Sherris, Jacqueline, , et al., ""Beyond our borders: cervical cancer in the developing world." Western Journal of Medicine 175(4): 231 (2001)".

Skala, Melissa C., , et al., ""Comparison of a physical model and principal component analysis for the diagnosis of epithelial neoplasias in vivo using diffuse reflectance spectroscopy." Optics Express 15(12): 7863-7875 (2007)".

Subhash, N., , et al., ""Oral cancer detection using diffuse reflectance spectral ratio R54QIR575 of oxygenated hemoglobin bands." Journal of Biomedical Optics 11(1): 014018-014018 (2006)".

Van Gemert, M. J. C., , et al., ""Skin Optics." Biomedical Engineering, IEEE Transactions on 36(12): 1146-1154 (1989)".

Vishwanath, Karthik, , et al., ""Portable, fiber-based, diffuse reflection spectroscopy (DRS) systems for estimating tissue optical properties." Applied Spectroscopy 65(2): 206-215 (2011)".

Wagadarikar, Ashwin A., , et al., ""Video rate spectral imaging using a coded aperture snapshot spectral imager." Optics Express 17(8): 6368-6388 (2009)."

Wang, Adrien, , et al., ""Targeting spectral signatures of progressively dysplastic stratified epithelia using angularly variable fiber geometry in reflectance Monte Carlo simulations." Journal of Biomedical Optics 12(4):044012.1-044012.14(2007)".

Warde, Padraig, , et al., ""T1/T2 glottic cancer managed by external beam radiotherapy: the influence of pretreatment hemoglobin on local control." International Journal of Radiation Oncology* Biology* Physics 41 (2): 347-353 (1998)".

Zeferino, Luiz Carlos, , et al., ""Cervical cancer in the developing world." Best Practice & Research Clinical Obstetrics& Gynecology 20.3: 339-354 (2006)".

Thekkek, Nadhi , et al., "Optical imaging for cervical cancer detection: solutions for a continuing global problem.", Nature Reviews Cancer 8.9 (2008): 725-731.

\* cited by examiner

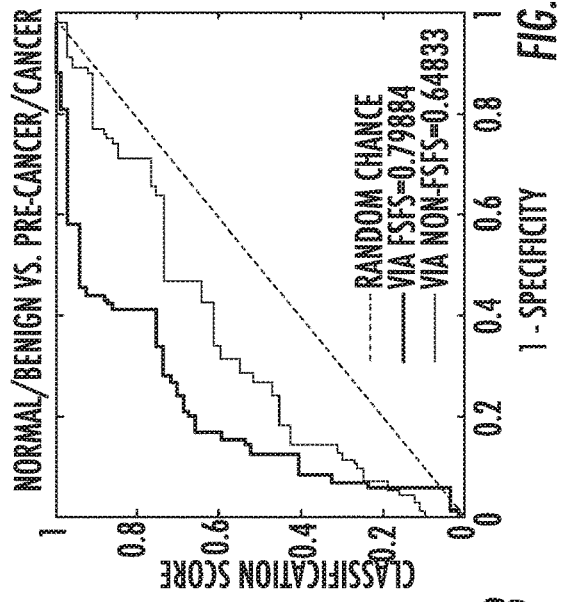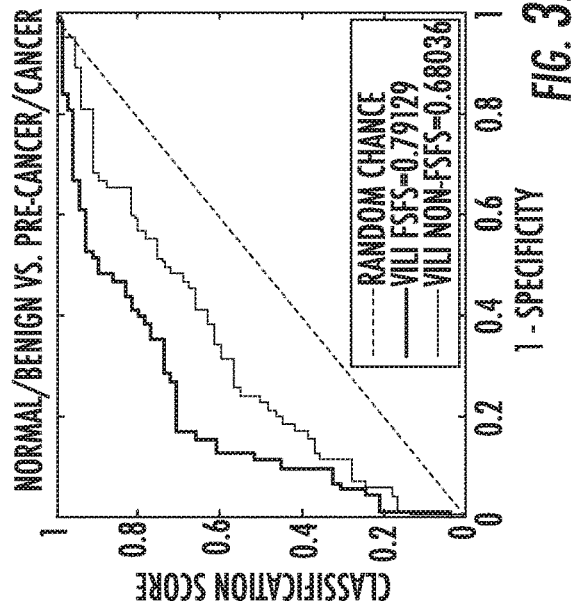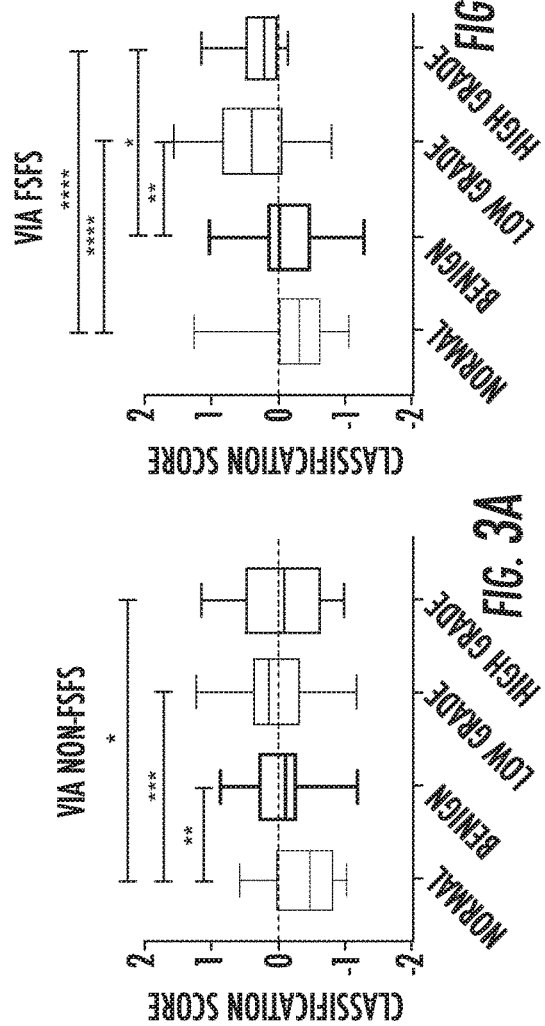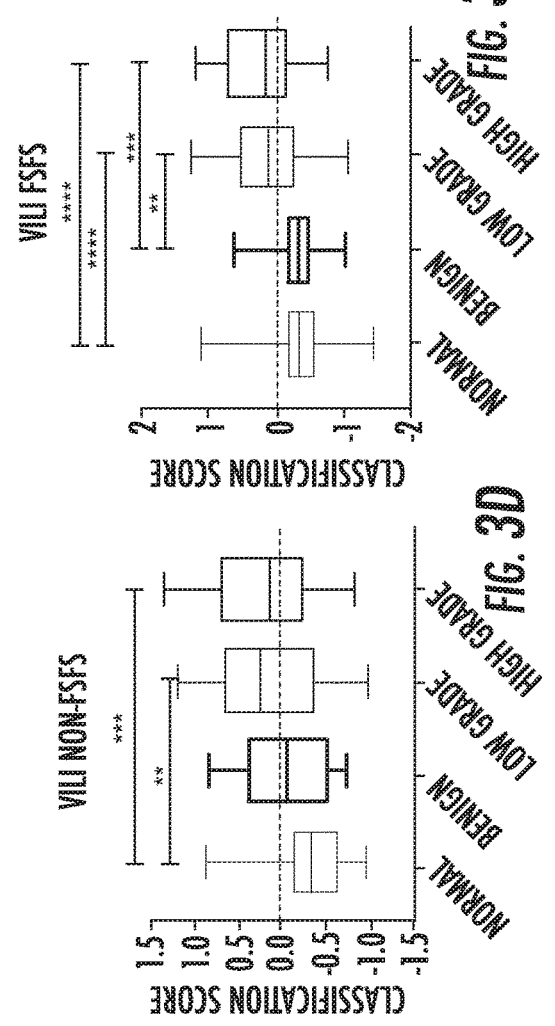

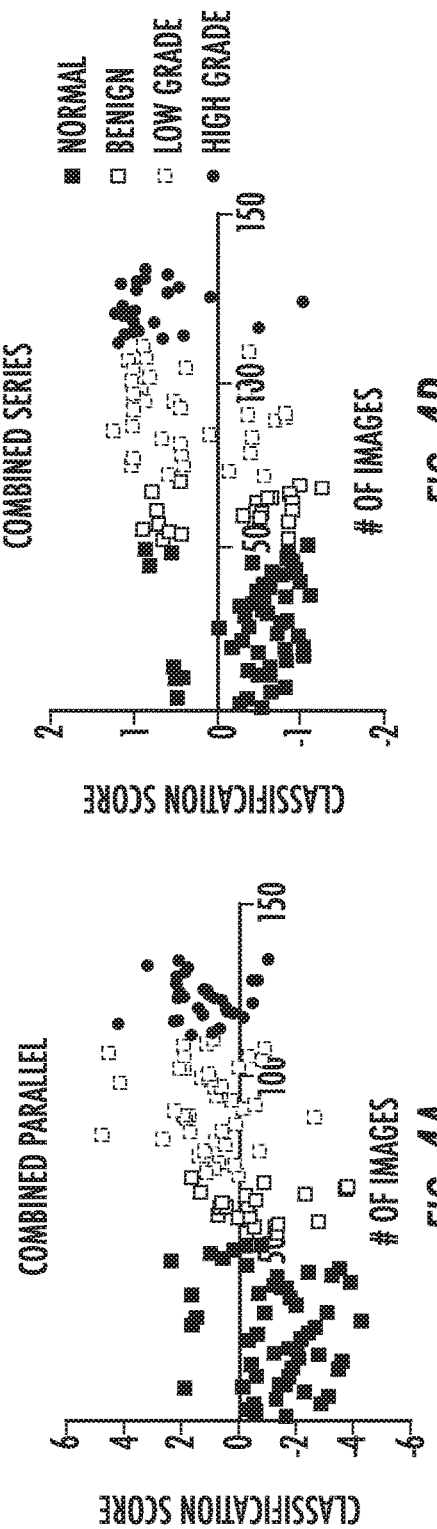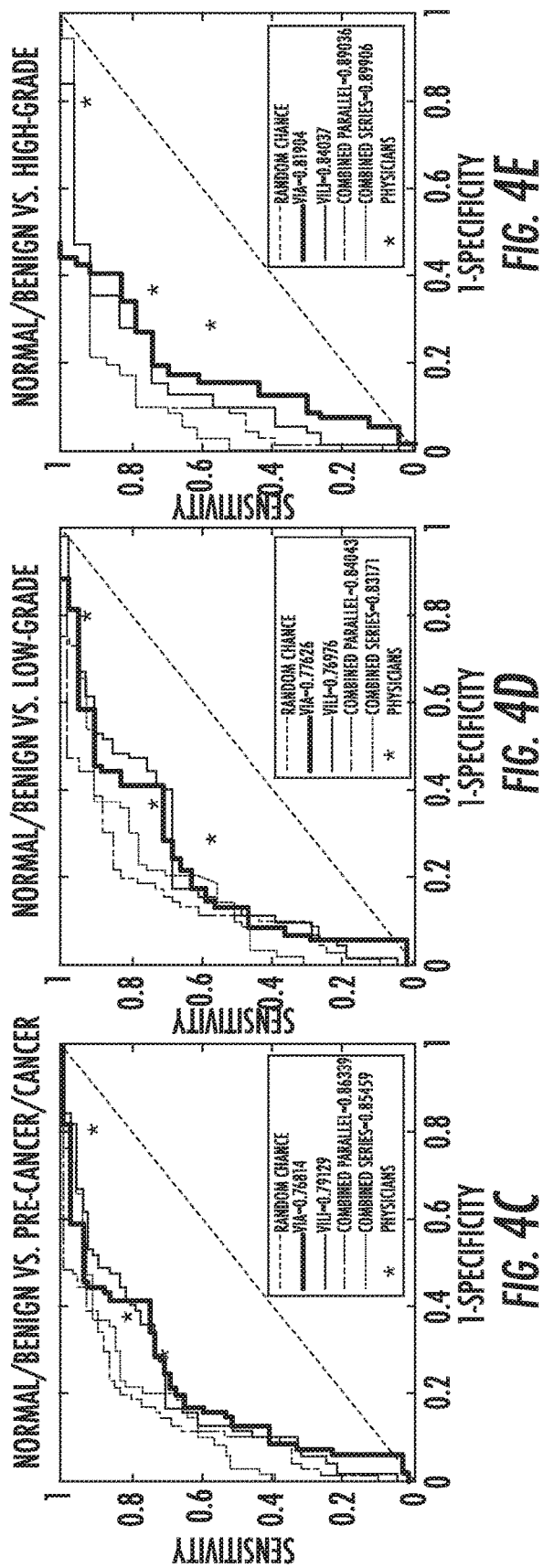
FIG. 4A  FIG. 4B  FIG. 4C  FIG. 4D  FIG. 4E

METHODS FOR AUTOMATED DETECTION OF CERVICAL PRE-CANCERS WITH A LOW-COST, POINT-OF-CARE, POCKET COLPOSCOPE

STATEMENT AS TO FEDERALLY SPONSORED RESEARCH

This work was supported in part by the U.S. National Institutes of Health under grant 1R01CA195500, the U.S. National Geospatial-Intelligence Agency under grant HM04761610001, the U.S. National Geospatial-Intelligence Agency under grant HM0177-13-1-0007, the U.S. Army Research Office under grant W911NF-16-1-0088, the U.S. National Science Foundation under grant NSF-CCF-13-18168, and the Allen Institute for Brain Sciences. The Government has certain rights in this invention.

RELATED APPLICATIONS

This application is a 35 U.S.C. § 371 national stage application of PCT International Application No. PCT/US2019/054773, filed Oct. 4, 2019, which application claims priority to U.S. Provisional Application No. 62/741,342, filed Oct. 4, 2018, the disclosures of which are hereby incorporated by reference herein in their entireties.

BACKGROUND

This work describes development of algorithms or methods to extract simple, yet powerful color and texture features from colposcopy images for VIA, VILI and GIVI contrasts. Features are used to train and validate a classifier for the individual contrast agents as well as for different combinations of the contrasts to assess improvement in performance. Towards this we hypothesize VIA algorithms developed can enable diagnostic accuracy on par with expert physicians (+/−5%). Including additional sources of contrast increases diagnostic accuracy on par with gold standard pathology (~80%).

In the United States and other high-income countries, cervical cancer incidence and mortality have decreased by 70% over the last 70 years; however, women living in low and middle-income countries (LMICs) still experience a disproportionately high burden of cervical cancer. In fact, about 85% of the global burden of cervical cancer occurs in LMICs, with 87% of cervical cancer related deaths occurring in these regions. In 2012, over 500,000 women were diagnosed with cervical cancer, and approximately 50% of them died from this disease. If status quo is maintained, the numbers are expected to rise to over 750,000 new cases and 400,000 deaths per year by 2035.

In high-resource settings, screening for cervical cancer is performed using a multi-tiered paradigm which begins with the Papanicolaou (Pap) smear with human papillomavirus (HPV) co-testing, followed by colposcopy guided biopsy and treatment if needed. Colposcopy uses a low-power microscope to visualize cervix changes that are highlighted with the application of exogenous contrast agents, such as acetic acid and in some cases Lugol's iodine. Acetic acid (3% or 5%) application to the cervix causes a reversible coagulation in nuclear proteins and cytokeratin, which primarily affect lesion areas due to high nuclear proteins content. This causes whitening and mosaic textured features in abnormal regions, whereas normal cervix regions remain a light pink color. Normal areas of the cervix are glycogen rich and take up Lugol's iodine, which turns normal cells dark brown, while abnormal areas are glycogen deficient and do not uptake the glycophilic Lugol's iodine solution and hence, appear pale/mustard yellow. Suspicious areas are biopsied for pathology confirmation of cervical abnormalities. Women with pre-cancer are treated via excision of a portion of the cervix using Loop Electrosurgical Excision Procedure (LEEP). Women with cancer are referred to a combination of local and/or systemic therapy depending on the stage of invasive disease. The screening model is not practical to implement in LMICs due to the resources that are required to procure and implement well-established solutions.

In low resource settings, HPV testing has been recommended as an alternative to the Pap smear. However, HPV testing is not widely available in LMICs, and if available, requires a secondary test that provides specificity in order to prevent large numbers of women from being unnecessarily referred for confirmatory testing or treatment. Visual inspection with acetic acid (VIA) using the naked eye is a low-tech version of colposcopy that serves to either add specificity to HPV testing (when available) or serves as the primary screening tool. However, VIA is not scalable for a number of reasons. Specifically, the lack of image capture results in poor quality control due to lack of documentation, and lack of magnification diminishes sensitivity to microscopic disease.

Our group has developed a low-cost, portable, point-of-care digital colposcope, called the Pocket Colposcope, to replace VIA with high-quality colposcopy, which is the established standard-of-care for triage in high-resource settings. An international study conducted by our group found high concordance between the Pocket Colposcope and standard-of-care clinical colposcopes. The Pocket Colposcope can overcome the limitations of VIA in settings where traditional colposcopes are too cumbersome and/or expensive to use. This will not only provide enhanced visualization and magnification compared to traditional VIA but will also provide much needed documentation and feedback to ensure quality control in healthcare provider performance. However, the limited availability of expert colposcopists in low resource settings represents yet another bottleneck. Therefore, our goal is to develop image processing and machine learning-based approaches for images obtained with the Pocket Colposcope to potentially recapitulate the expertise of an experienced colposcopist in settings where there is a shortage of experts available to screen large populations.

Several groups working on algorithms for automated computer-aided colposcopy have shown proof-of-concept image analysis and classification to automatically interpret acetowhitening for cervical cancer detection. These methods have been predominantly applied to VIA cervigrams only, which do not fully capture all sources of contrast described in the modified Reid's Colposcopic Index (mRCI). Additionally, most of these methods require pre-selection of suspicious regions (semi-automated), use physician labels for ground truth rather than gold-standard pathology, and have not been demonstrated to be scalable, particularly since these methods still rely on subjective user interpretation. Visual inspection with Lugol's iodine (VILI), which provides another important source of contrast for the visualization of cervical abnormalities, has not been evaluated previously. Studies with physicians providing diagnosis based on both contrasts have shown that VILI has the potential to bolster the performance of algorithms based on VIA alone.

However, other studies have found that while the parallel combination of VIA and VILI bolsters sensitivity, it reduces specificity.

Recently, deep learning methods have been explored for classifying cervigrams and other cancer imaging applications, such as endoscopy. Xu et al. used a multimodal convolutional neural network with inputs from a combination of (1) physician interpretation of 10,000 colposcopy images, and (2) patient clinical records (age and pH value, Pap smear cells, HPV signal and status) to a provide a cervical pre-cancer/cancer classification model with 88.91% accuracy, 87.83% sensitivity, and 90% specificity. However, limitations include the need for a large data set (10,000 images), and the use of Pap and HPV information, which may not be available, particularly in low-resource settings where incidence and mortality are highest. Additionally, in most prior studies physician diagnosis was used as ground truth for training classifier on image interpretation, which introduces human subjectivity present in colposcopy. In endoscopy, another internal imaging technique, deep learning has been used for computer aided diagnoses in recognizing and identifying polyps and tumors.

Even though deep learning has a huge potential application in medical imaging for accurate computer-aided diagnosis (and has seen recent successes in FDA cleared technologies), its application has yet to scale up due to the lack of large datasets comprised of accurately annotated images that transfer across acquisition devices and protocols. Though these barriers listed can be overcome for cervical colposcopy applications, it will require time, cost, and availability of resources for pathological annotation. Studies have proposed image data generation methods to overcome the obstacle of large data sets needed for deep learning. Though these methods have promise for future applications, they are currently not viable for our application. Finally, domain specific features exploited here are more explainable than those often obtained from deep-learning, and this is critical both for adoption by providers and identifying clinical steps following screening.

While some recent tools such as U-NET have demonstrated to be very general for numerous medical imaging tasks, the goal of this work is not to introduce a powerful, generic algorithm, but to use domain knowledge to solve a very specific and important challenge: automatic screening of cervical pre-cancers. We will demonstrate that with a relatively simple, computationally efficient, and explainable tool we achieve expert-level diagnosis with limited training data. Some of the lessons learned from the proposed technical contribution could potentially benefit other medical image segmentation and screening applications, when properly combined, as done here, with domain knowledge and other more generic tools.

SUMMARY

Some embodiments of the present invention are directed to a method for automated detection of cervical pre-cancer. The method includes: providing at least one cervigram; pre-processing the at least one cervigram; extracting features from the at least one pre-processed cervigram; and classifying the at least one cervigram as negative or positive for cervical pre-cancer based on the extracted features.

In some embodiments, the pre-processing step includes applying specular reflection attenuation to reduce specular reflection in the at least one cervigram.

In some embodiments, the pre-processing step includes cropping the at least one cervigram to remove clinically insignificant features such as a speculum or vaginal walls. The cropping step may include automatically cropping the at least one cervigram.

In some embodiments, the pre-processing step for feature extraction includes automatically segmenting a region from the cervix for further analysis. The automatically segmenting step may be carried out using a Gabor filter. The segmented region may have the highest mean Gabor response.

In some embodiments, the extracting step includes extracting texture based features. The extracting step may include calculating Haralick's features including contrast, correlation, energy, and homogeneity for the segmented region. The extracting step may include transforming the segmented region to different color spaces and, for each color channel of each color space, calculating central tendencies of mean, median, mode, and variance and Otsu threshold level. The at least one cervigram may include a VILI image, and the extracting step may include determining a pseudo lesion size based on the concentration of or the percentage of pixels corresponding to the yellow staining from non-uptake of Lugol's iodine.

In some embodiments, the at least one cervigram includes corresponding VIA and VILI images, and the classifying step is carried out using a classification algorithm for VIA only images and a classification algorithm for VILI only images. The classifying step may be carried out using a parallel-combined algorithm, and prediction scores for classifying the VIA and VILI images with their respective algorithms may be input as predictors to generate a classifier model for a combined classification. The classifying step may be carried out using a serial-combined algorithm including: applying the classification algorithm for VIA only images to the VIA image to identify the VIA image as VIA negative or VIA positive; classifying the corresponding VIA and VILI images as negative if the VIA image is identified as VIA negative; if the VIA image is identified as VIA positive, applying the classification algorithm for VILI only images to the VILI image to identify the VILI image as VILI negative or VILI positive; classifying the corresponding VIA and VILI images as negative if the VILI image is identified as VILI negative; and classifying the corresponding VIA and VILI images as positive if the VILI image is identified as VILI positive.

In some embodiments, the at least one cervigram includes corresponding VIA and GIVI images, and the classifying step is carried out using a classification algorithm for VIA only images and a classification algorithm for GIVI only images.

In some embodiments, the at least one cervigram includes corresponding VIA, VILI, and GIVI images, and the classifying step is carried out using a classification algorithm for VIA only images, a classification algorithm for VILI only images, and a classification algorithm for GIVI only images.

Some other embodiments of the present invention are directed to a method for developing an algorithm for automated cervical cancer diagnosis. The method includes: providing a plurality of cervigrams; pre-processing each cervigram; extracting features from each pre-processed cervigram; and establishing a classification model based on the extracted features for each cervigram. The classification model is configured to classify additional cervigrams as negative or positive for cervical pre-cancer.

In some embodiments, the pre-processing step includes applying specular reflection attenuation to reduce specular reflection in each cervigram.

In some embodiments, the pre-processing step includes cropping at least some of the plurality of cervigrams to remove clinically insignificant features such as a speculum or vaginal walls. The cropping step may include automatically cropping the at least some of the plurality of cervigrams.

In some embodiments, the pre-processing step for feature extraction includes automatically segmenting a region from the cervix for further analysis. The automatically segmenting step may be carried out using a Gabor filter. The segmented region may have the highest mean Gabor response.

In some embodiments, the extracting step includes extracting texture based features. The extracting step may include calculating Haralick's features including contrast, correlation, energy, and homogeneity for the segmented region.

In some embodiments, the extracting step includes transforming the segmented region to different color spaces and, for each color channel of each color space, calculating central tendencies of mean, median, mode, and variance and Otsu threshold level.

In some embodiments, at least one or some of the plurality of cervigrams includes a VILI image, and the extracting step includes determining a pseudo lesion size based on the concentration or percentage of pixels corresponding to the yellow staining from non-uptake of Lugol's iodine.

In some embodiments, the establishing step includes selecting an optimal subset of the extracted features for each cervigram for optimal training and to prevent over fitting of the classification model. The selecting step may be carried out using forward sequential feature selection that considers redundancy of feature selection as well as feature interaction.

In some embodiments, the establishing step includes regularization of the extracted features to prevent overfitting or underfitting.

In some embodiments, the plurality of cervigrams include corresponding VIA and VILI images, and the establishing step is carried out using a classification algorithm for VIA only images and a classification algorithm for VILI only images. The establishing step may be carried out using a parallel-combined algorithm, and prediction scores for classifying the VIA and VILI images with their respective algorithms may be input as predictors to generate the classification model for a combined classification. The establishing step may be carried out using a serial-combined algorithm including: applying the classification algorithm for VIA only images to the VIA image to identify the VIA image as VIA negative or VIA positive; classifying the corresponding VIA and VILI images as negative if the VIA image is identified as VIA negative; if the VIA image is identified as VIA positive, applying the classification algorithm for VILI only images to the VILI image to identify the VILI image as VILI negative or VILI positive; classifying the corresponding VIA and VILI images as negative if the VILI image is identified as VILI negative; and classifying the corresponding VIA and VILI images as positive if the VILI image is identified as VILI positive.

In some embodiments, the plurality of cervigrams include corresponding VIA and GIVI images, and the establishing step is carried out using a classification algorithm for VIA only images and a classification algorithm for GIVI only images. The establishing step may be carried out using a parallel-combined algorithm, and prediction scores for classifying the VIA and GIVI images with their respective algorithms may be input as predictors to generate the classification model for a combined classification. The establishing step may be carried out using a serial-combined algorithm including: applying the classification algorithm for VIA only images to the VIA image to identify the VIA image as VIA negative or VIA positive; classifying the corresponding VIA and GIVI images as negative if the VIA image is identified as VIA negative; if the VIA image is identified as VIA positive, applying the classification algorithm for GIVI only images to the GIVI image to identify the GIVI image as GIVI negative or GIVI positive; classifying the corresponding VIA and GIVI images as negative if the GIVI image is identified as GIVI negative; and classifying the corresponding VIA and GIVI images as positive if the GIVI image is identified as GIVI positive.

In some embodiments, the plurality of cervigrams include corresponding VIA, VILI, and GIVI images, and the establishing step is carried out using a classification algorithm for VIA only images, a classification algorithm for VILI only images, and a classification algorithm for GIVI only images. The establishing step may be carried out using a parallel-combined algorithm, and prediction scores for classifying the VIA, VILI, and GIVI images with their respective algorithms may be input as predictors to generate the classification model for a combined classification.

In some embodiments, the establishing step is carried out using a support vector machine classifier, a logistic regression classifier, or a neural network classifier.

Some other embodiments are directed to a computer program product for automated detection of cervical pre-cancer. The computer program product includes a non-transitory computer readable storage medium having encoded thereon instructions that, when executed on a processor, cause the processor to perform the methods as described above.

Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIGS. 3A-3F compare results of classification scores for VIA and VILI images achieved using features selected from the simple filter selection method and the forward sequential feature selection (FSFS).

FIGS. 4A-E illustrate the performance of different classification algorithms.

DETAILED DESCRIPTION

Figure 1:
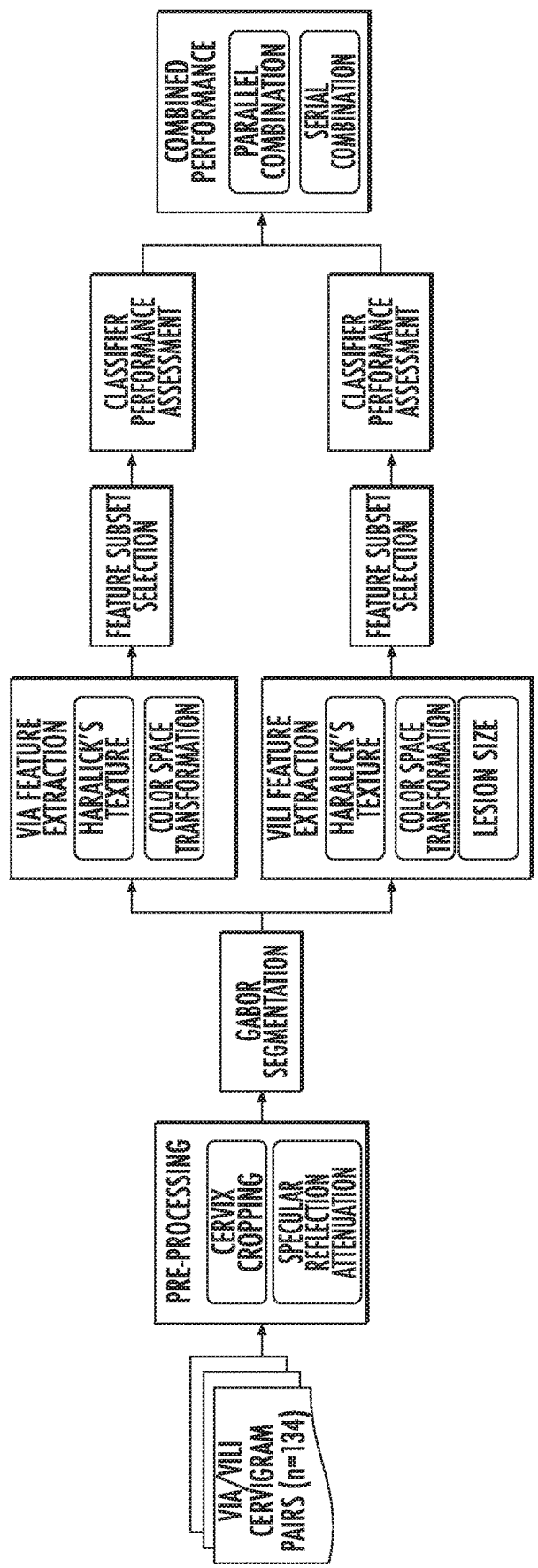
FIG. 1 is a flow chart illustrating operations to develop an algorithm for automated detection of cervical pre-cancers according to some embodiments of the present invention.

One of our goals is to develop a series of feature extraction and machine algorithms that leverage both VIA and VILI images obtained with Pocket Colposcope for the automated diagnosis of cervical pre-cancers to recapitulate expert colposcopist performance. By developing a novel strategy incorporating VILI algorithms, we hypothesize we can achieve improved sensitivity and specificity performance over VIA alone. Unlike previous approaches, this method uses pathology gold standard labels for training and does not require a health provider to pre-select an area of concern, but rather evaluates the entire cervix to automatically identify regions of interest. The algorithms work by pre-processing images to reduce specular reflection, automatically segmenting a region of interest from the cervix for analysis, extracting color- and texture-based features, and using a support vector machine for binary classification of VIA and VILI images. Receiver operating characteristics (ROC) curves are generated from the classifier to determine the area under the curve (AUC), which indicates how well a model predicts classes. VIA and VILI algorithms were then combined. With the proposed framework, the best performing model used the combined VIA and VILI and achieved sensitivity of 81.3%, specificity of 80.0%, and overall AUCs of 0.86, compared to pathology. As a point of comparison, expert physicians' interpretation achieved an average sensitivity of 77% and specificity of 51% for the same dataset.

We have also developed a series of feature extraction and machine algorithms that leverage VIA, VILI and GIVI (green illumination vascular imaging) images obtained with Pocket Colposcope for the automated diagnosis of cervical pre-cancers to recapitulate expert colposcopist performance. By developing a novel strategy incorporating VILI and GIVI algorithms, we hypothesize we can achieve improved sensitivity and specificity performance over VIA alone. Unlike previous approaches, this method uses pathology gold standard labels for training and does not require a health provider to pre-select an area of concern, but rather evaluates the entire cervix to automatically identify regions of interest. The algorithms pre-process images to reduce specular reflection, automatically segments a region of interest from the cervix for analysis, extracts color- and texture-based features, and utilizes a support vector machine for binary classification of VIA, VILI and GIVI images. Receiver operating characteristics (ROC) curves are generated from the classifier to determine the area under the curve (AUC), which indicates how well a model predicts classes. VIA, VILI and GIVI algorithms are then combined using methods explained further below. With the proposed framework, we demonstrate that individually, algorithms perform on par expert physicians' interpretation but when features are combined, algorithms could potentially significantly improve diagnostic accuracy.

Our main contributions are summarized in the following three areas and their complete integration.

An overall real-time, simple, efficient, and repeatable algorithm which utilizes established approaches in image processing and machine learning to classify cervical cancer images. Classification is performed for individual contrasts, and combinations of these contrasts with high accuracy and speed are compared to expert colposcopists. We develop algorithms for acetic acid only, Lugol's iodine only, GIVI only and different combinations of the two and show a synergistic improvement in performance, compared to using one source of contrast. To the best of our knowledge, this is the first work extracting and combining explainable features from acetic acid and Lugol's iodine images for cervical cancer classification. The proposed methods for combining contrasts can be potentially applied to other imaging modalities, specifically, clinical colposcopes that use more than one source of contrast for diagnosis.

This method is different from other methods for cervical cancer image classification that require preselection of suspicious regions of the cervix, or use physician interpretation as ground truth, which introduces subjectivity and human error. In previous published studies, a region of the cervix is manually selected and then further analyzed for classification. In our study, we automatically segment a region of interest using Gabor filters and then further analyze the segmented regions for color and texture. Additionally our classifier is trained using gold-standard pathology as ground truth rather than physician interpretation.

The Pocket Colposcope used in this study is unique compared to other colposcopes in its ability to acquire an image an inch away from the cervix, remove a majority of the noise (speculum, vaginal walls), and consequently decrease the level of image processing complexity required for cervix segmentation, which has been documented in previous methods. When combined with the algorithms introduced here, the Pocket Colposcope could enable widespread scalable screening for cervical cancer. The Pocket Colposcope is described in more detail in PCT International Publication No. WO/2019/070998 to Ramanujam et al., later published as U.S. Publication No. _____, the disclosure of which is incorporated by reference herein in its entirety.

Methods

First, VIA and VILI images from the Pocket Colposcope were cropped to remove clinically irrelevant features such as the speculum, vaginal walls and specular reflection automatically attenuated. For both VIA and VILI images, a Gabor filter was applied to automatically segment regions within the cervix for further analysis based on color and texture differences. Haralick's features (contrast, correlation, energy and homogeneity) were calculated from these segments. The segments were also transformed to different color spaces (grayscale, RGB, YCbCr, HSV and CIElab). From each color space central tendencies, mean, median, mode, variance and Otsu threshold level were calculated for each color channel of each color space. Additionally, for VILI images the percentage of pixels corresponding to the yellow staining from non-uptake of Lugol's iodine by the lesion region was used to determine a pseudo lesion size. An optimal subset of these features was selected using a wrapper forward sequential feature sub-selection for the individual VIA and VILI algorithms. These features were used to train a support vector machine (SVM) classifier using pathology as ground truth labels, and 5-fold cross validation was used to determine performance and generate ROC curves for binary classification of images as VIA/VILI positive or negative. For the parallel-combined algorithm, scores for classifying the VIA and VILI images with their respective algorithms were input as predictors to generate a classifier for combined classification. For the serial-combined algorithm, the VIA algorithm with selected features was first applied to the VIA image data set at a threshold set to enable high sensitivity which resulted in high positivity rate. VIA negatives were classified as negatives by the algorithm while VIA positives were further analyzed with the VILI algorithm. Corresponding VILI images of the VIA positives were analyzed with the VILI algorithm (which has higher specificity) for binary classification as negative or positive. Results for VIA only, VILI only and the combined methods were compared to each other and to the performance of expert physicians on the same data set. FIG. 1 provides a summary of the steps of the individual VIA and VILI algorithms described, which is further described below. It is important to note that the algorithm uses a combination of domain-knowledge inspired features with machine learning, since unlike other applications which use neural networks, the amount of training data is limited.

FIG. 1 is a flow chart of the individual feature extraction and classification processes. Image collection: A low-cost, Pocket Colposcope for cervix imaging was used to obtain 134 image pairs of acetic acid (VIA) and Lugol's iodine contrasts (VILI). Pre-processing: These images were pre-processed by applying a specular reflection attenuation algorithm to remove bright white speckles. Custom Gabor filters were applied to the image to select a region of interest for further processing. The preprocessing and segmentation stages were the same for both VIA and VILI. Feature extraction: For VIA pre-processed images, Haralick's texture features, including contrast, correlation, energy and homogeneity, were obtained. Images were also transformed into individual channels of different colorspaces, overall generating 69 features for each VIA image. For VILI images, the same Haralick's texture and color features were extracted, however approximate lesion stain size was also determined, yielding 70 features. A subset of these features were selected with a wrapper feature selection method and selected features were used to train and cross-validate a support vector machine. Finally, the features from VIA and VILI were combined using 2 different methods: e) Parallel method and f) Serial method. These were validated to determine improvement of combined classification over using one source of contrast alone.

A. Image Collection

Images and labels were retrospectively obtained from a database of Pocket Colposcope images acquired in a previous clinical study in which blinded expert physicians provided a diagnosis for each patient from reviewing randomized digital cervigrams based on both VIA and VILI images.

To summarize, two hundred patients undergoing colposcopy examination at La Liga Contra el Cancer Clinic in Lima, Peril were recruited for a clinical study. This study was approved by Duke University institutional review board and performed with approved protocol, informed consent process, and data storage system at La Liga Contra el Cancer, Lima, Peru. For each patient, acetic acid was applied to the cervix and images were captured with the standard-of-care colposcope followed by the Pocket Colposcope. Lugol's iodine was then applied to the cervix and VILI images captured with the standard-of-care colposcope followed by the Pocket Colposcope. Images, patient demographics, and pathology results were collected and stored in a HIPAA compliant secured database REDcap. No biopsies were taken for normal colposcopies as per standard-of-care procedures. Hence the ground truth for VILI negative images was primarily based on expert physician interpretation. Of biopsies taken based on positive colposcopy, 6 came back normal, 19 came back as benign conditions (cervicitis and condilomas) and the remainder were pre-cancers (CIN1, CIN2+) or cancers (invasive carcinomas). For algorithm binary classification labels, condilomas and cervicitis were considered pathologically normal. 25 out of 51 (49%) colposcopy-negatives were pathology-confirmed negative and 26 out of 51 (51%) were negative based on interpretation by the lead colposcopist at the clinic. VIA/VILI image pairs which were deemed interpretable by an expert physician were randomized and sent out to three expert colposcopists for cervical pre-cancer diagnosis. Physician interpretation was based on both VIA and VILI features and were classified as either VILI/VIA positive or negative.

B. Cervix Pre-Processing

Cervix cropping. Cervigrams typically contain clinically superfluous features such as the vaginal sidewalls and the speculum. These artifacts can affect feature extraction and diagnostic accuracy of an automated algorithm and therefore were removed to enable accurate analysis and classification of features pertaining to the cervix. Due to image positioning diversity which for each cervigram, the cervix region of interest (ROI) was cropped using a minimum bounding box around the cervix region identified by an expert colposcopist. With standardized images in which the cervix took up about 90% of the image, no cropping was necessary.

Specular reflection attenuation. Specular reflections appear as bright white spots on the cervigram where there is saturation of light exceeding the camera's linear detection range for a set exposure. Specular reflections from Pocket Colposcope images were primarily caused by moisture, the uneven surface of the cervix, excess light illumination, and for the VILI images light reflecting off the dark VILI stains. Specular reflection affects subsequent processing methods, which are primarily color-based, hence the need to attenuate their effect. We employed the well-established specular reflection attenuation method described by A. Das, Avijit Kar, and Debasis Bhattacharyya, "Elimination of specular reflection and identification of ROI: The first step in automated detection of Cervical Cancer using Digital Colposcopy," *Imaging Systems and Techniques* (*IST*), 2011 *IEEE International Conference on. IEEE,* 2011. In summary, the raw RGB image was separated into the R, G, and B channels. Specular reflection was identified by finding pixels above a threshold (220 for an 8-bit image) from each channel and logically AND-ing them. In the binary image, the outlines of reflection were dilated, and the borders of dilated outlines were identified on the original image. A Laplacian infill method using values from these borders was used to smoothly interpolate inward from the border pixels, providing an output image with reduced specular reflection.

Gabor segmentation. A Gabor algorithm combined with k-means clustering was applied to the grayscale of the raw RGB image to select a region within the cervix for further analysis. Gabor filters look for specified frequency content in an image in specified regions and directions, similar to the human visual system. Our hypothesis was that the Gabor filter would have a high frequency response within the acetowhite/texturized regions in VIA positive and yellow lesion regions in VILI positives. K-means clustering, an unsupervised learning method which splits unlabeled data into k number of clusters, was then used to segment the Gabor filtered image into two clusters, and the cluster with the higher Gabor mean selected for further analysis. For VIA/VILI negative regions, the assumption was that a region within the cervix would be selected for further analysis, which would subsequently indicate negativity. Utilizing this approach overcomes limitation from previous studies where regions needed to be manually selected for further textural analysis. A multi-scale Gabor filter was created with different orientations (0, 45, 90, 135 degrees) and different wavelengths in increasing powers of two starting from $4\sqrt{2}$ up to the hypothenus length of the input image. The orientations and wavelengths used in this study are well established for unsupervised texture segmentation.

The filter was convolved with each image to obtain the overall Gabor response. K-means clustering (k=2) was used to segment the cervix into two regions based on the Gabor response. The region with the highest mean Gabor response was selected for further analysis. Gabor segmented regions were used to calculate color, and Haralick's texture features were used for both VIA and VILI images. Pseudo lesion size was also calculated for VILI images.

C. Feature Extraction

Haralick's texture features. Since acetic acid application causes textured mosaicism, which highlights different vasculature patterns corresponding to different diagnosis, we calculated Haralick's texture features to analyze the Gabor-segmented VIA regions. This method was also applied to VILI images with the assumption that since VILI is applied after VIA, there may be texturized regions within the VILI segments. In the greyscale image, we calculated the grey-level co-occurrence matrix (GLCM), a second order statistical method which characterizes an image by calculating how often a pair of pixels with specific values and spatial relationship occur in an image. The GLCM was computed for four different pixel offsets (1, 5, 10 and 15) each in four different directions (0, 45, 90, 135 degrees), for a total of 16 matrices. Small to medium offset values were used since we expected mosaicism features to show pixel differences within this range. The different directions were used since features of interest may be horizontal, vertical or diagonal. From these GLCMs, four Haralick's features were calculated: contrast, correlation, energy and homogeneity were calculated. This yielded 4 texture-based features for each VIA and VILI image.

Color space transformation calculations. According to the mRCI, both VIA and VILI cervigram classification are primarily based on staining. For VIA, acetowhitened regions correspond to lesions, while light pink regions correspond to normal epithelium. For VILI, yellow regions correspond to lesions, while darker brown staining corresponds to normal epithelium. Based on this biological effect explained in detail in the introduction, color-based features were extracted. Each image was transformed to five different color spaces and these separated into individual color channels, specifically 'Red(R), Green(G), Blue(B) (RGB)', 'grayscale', 'Hue(H), Saturation(S), Value(V) (HSV)', 'Luminance(Y), blue chroma(Cb) and Red chroma(Cr) (YCbCr)', and 'Lightness(L), red/green(a), and yellow/blue (b) (CIELAB)'. RGB color space is widely used for digital image acquisition; however, one of its primary disadvantages is that it is device dependent and sensitive to illumination differences, which limits the use for color-based image analysis. CIELAB color space extends the RGB color space from 90% to 100% of all perceivable colors and enables more quantitative applications since it correlates to perceptual descriptors of color. Additionally, CIELAB and the YCbCr color spaces separate image luminous intensity from color information, reducing factors resulting from how an image was taken, such as variations in LED brightness. HSV rearranges the geometry of RGB color space to make it more intuitive and perceptually relevant, separating color based of its hue, saturation and lightness. Gray scale of an RGB image has luminance information of the image.

For each color channel, we determined summary central tendencies of mean, median, mode, and variance. Otsu threshold level (two-class classification) was also determined on color-space transformed images to take advantage of multiple clusters present from the brown normal regions and yellow abnormal regions. The Otsu threshold is a widely used, nonparametric, unsupervised method, which automatically selects a threshold to separate an image into two clusters, maximizing inter-class variance and minimizing intra-class variance. From each of the thirteen channels of the different color space transforms, the mean, median, mode, variance, and Otsu's threshold were extracted as potential classification features. Overall 65 color-based features were extracted for each VIA and VILI image.

Lesion size determination. A pseudo lesion size detection was performed for VILI images after Gabor segmentation. Due to the high variation in acetowhitening lesion and normal epithelium shades, it was not possible to determine lesion size for VIA images based on acetowhitening alone. Since VILI images provide a higher, more consistent contrast between dark brown normal epithelium and yellow stained abnormal epithelium, color-based "pseudo lesion size" was determined using VILI images. VILI images were transformed into CIElab color space explained previously and the b channel was extracted due to its direct linearity of yellow shades and high contrast in color transforms. A threshold was determined via analysis of pixel intensities of ROIs from a subset of images corresponding to lesions and non-lesion regions. The number of pixels above this threshold was divided by the total number of pixels in the bounded cervix region to approximate a percent "lesion size". We call it pseudo lesion size because Lugol's iodine solution may also result in yellowing due to non-uptake in benign cervical conditions, such as condilomas, cervicitis. Parts of the cervix where Lugol's Iodine is not properly applied (such as cervix boundaries) also show non-uptake yellow features. This resulted in overall a total of 70 features for VILI and 69 features for VIA images.

D. Feature Selection, Classifier Training and Testing

Classifier design. We selected a support vector machine classifier, a widely used and successful supervised learning method, which outputs an optimal hyperplane for classification. SVM parameters are as follows:

Predictor standardization: Predictors standardized using their corresponding weighted means and weighted standard deviations. Kernel function: Gaussian or RBF.

$$G(xj,xk)=\exp(-\|xj-xk\|2) \quad (1)$$

Kernel Scale: ~1.008 by automatic appropriate scale factor determined using a heuristic procedure. This heuristic procedure uses subsampling, so estimates can vary from one call to another.

Solver: ISDA Iterative Single Data Algorithm

Kernel offset: 0.1

For standard classifier training, a labeled training data set is input into the classifier which then builds a model to enable classification of a new data set. For non-linearly separable data sets, the SVM can transform data points to higher dimensions to linearize them for optimal separation using higher order kernels. From initial scatter plots demonstrating non-linearity of the data set, we selected a Radial Basis Function (RBF or Gaussian) kernel with automatically selected kernel size using cross validation. RBF kernel was selected because it is most widely used due to flexibility and ability to project data into high (infinite) dimensionality space to find a linear separation. The features were used as predictors while the pathology diagnosis (normal and benign vs. CIN+) was used as input labels for binary classification. While other machine learning tools could potentially be used, SVM was selected due to the limited data available for training and its excellent performance as reported below.

Feature selection and validation. In machine learning, classifying data using a proportionally high number of features compared to sample size can result in classifier failure due to redundancy and overfitting or overtraining to noise/artifacts. High feature number also increases storage and computational requirements. Due to a limited sample size (n=134 VIA/VILI pairs), a small subset of important features for satisfactory classification performance was selected using forward sequential feature selection (FSFS) with minimum classification error (MCE). The FSFS is a fast, wrapper feature selection method, in which feature candidates are sequentially added to an empty set until there is no further improvement in prediction. For each feature subset, the function performs a 5-fold cross validation with the classifier. The feature number and combination, which provided the minimum error for classification is then selected.

Training and testing. The optimal feature subset was used as predictors into the SVM to generate a classification model which was validated using 5-fold cross validation with pathology as ground truth (note that pathology is not available even to clinicians doing visual observation, so this ground truth is a very high standard). For cross validation for VIA and VILI features, the data set was divided into 5. Training was performed on ⅘ of the data and testing performed on the remaining ⅕ of the data. This was repeated leaving a different data set each time and the results averaged. ROCs were generated to determine the AUC, and sensitivity and specificity of each the algorithm was compared to physician performance for classifying images as negative or positive.

E. Combining VIA and VILI Features

Parallel combination. When the SVM classifier classifies VIA and VILI images as negative and positive it also assigns a score to each image which describes the probability or likelihood that the label comes from one of the classes. These probabilities for VIA and VILI images were used as predictor inputs into the parallel-combined SVM classification model with binary pathology labels. A classification model was then generated from these to provide binary classification based on both VIA and VILI inputs.

Serial combination. For serially combining VIA and VILI results, we analyzed the data from the individual VIA and VILI algorithms to determine where they complemented each other. Based on this analysis, we first ran the VIA algorithm, using the same feature subset on all images with a low classification cutoff (−0.25 instead of 0) for binary classification. This enabled classification of all high grades but also resulted in a high false-positivity rate. Negatives based on this classification were considered true negatives. The VILI algorithm was then run on the VIA positive images to increase specificity. An SVM classifier model was generated for the VIA and then VILI stage and cross-validated with pathology as ground truth.

Results

A. Image Breakdown

Of the 200 Pocket Colposcope patients, 66 were excluded due to one or more of the following factors: screen fail (2.5%), missing pathology for ground truth (2%), images not saved (missing) (6%), blurriness (10%), and device set at the wrong working distance (7%). Device related issues have been addressed in a newer version of the Pocket Colposcope design and improved control software. For the purpose of this study, data from a total of 134 patients were used for image analysis. The pathology distribution of patient whose cervigrams were utilized for the study are outlined in Table I.

TABLE I

Image Pathology Distribution

| VIA/VILI classification | Pathology Classification | # of patients (%) |
| --- | --- | --- |
| Negative | Normal | 51 (38%) |
|  | Cervicitis | 17 (13%) |
|  | Condiloma | 2 (0.01%) |
| Positive | CIN1 | 41 (31%) |
|  | CIN2 | 10 (0.07%) |
|  | CIN3 | 5 (0.04%) |
|  | Invasive Cancer | 8 (0.06%) |

B. Image Processing and Feature Extraction

Figure 2:
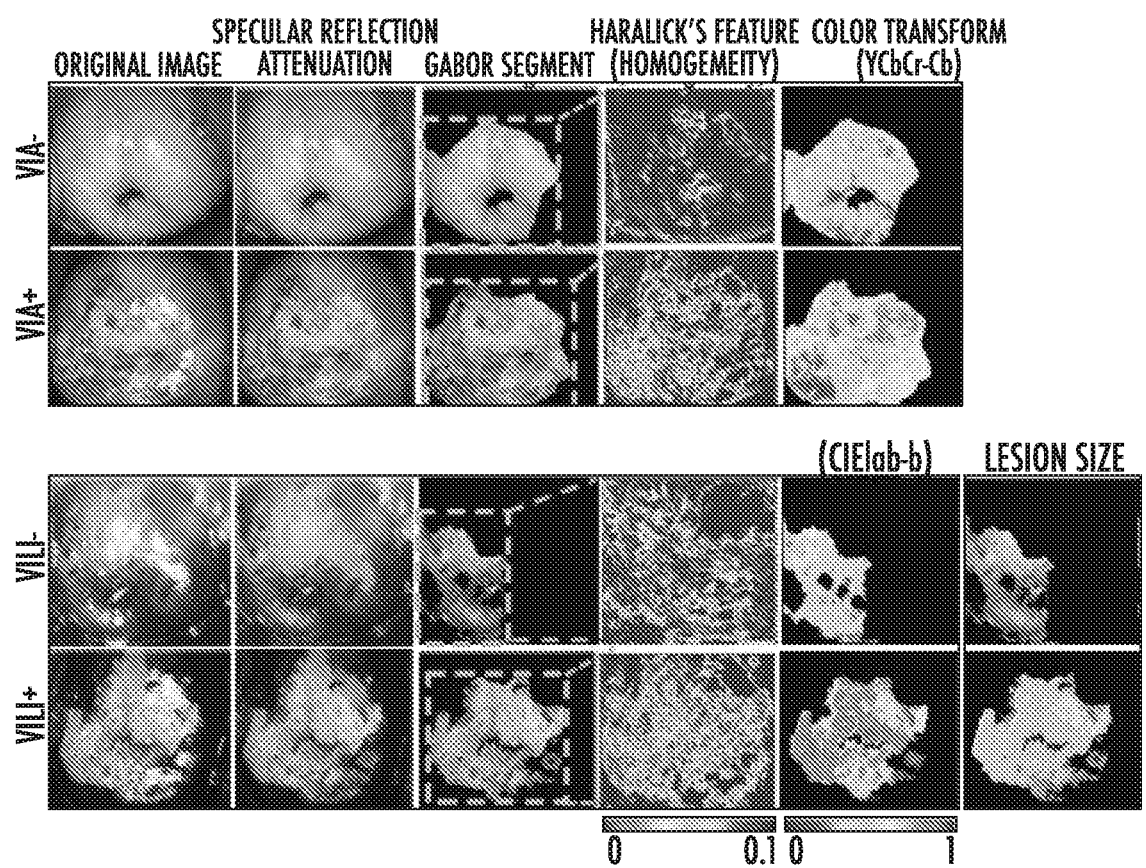
FIG. 2 illustrates endpoints for feature extraction methods used for VIA and VILI classification according to some embodiments of the present invention.

Specular reflection attenuation. Pre-processing to attenuate specular reflection was performed prior to feature extraction and classification to prevent inaccuracies due to glare. FIG. 2 shows results from representative images with specular reflection before and after specular reflection attenuation. Due to the speckled nature of specular reflection it is difficult to accurately hand select all glare regions for quantitative comparison and analysis of reduction. However, upon visual inspection all images had significantly reduced specular reflection without affecting contrast in the images. This finding is similar to previous work in this area.

Gabor Filtering. A Gabor filter was applied to pre-processed VIA/VILI images and the response normalized. Lesion regions for both VIA and VILI Images had higher Gabor responses than the surrounding epithelium. Images were segmented into two main regions by k-means clustering (k=2) and the region with highest mean Gabor response selected. Since VIA and VILI negative images had no or little acetowhitening/yellowing, regions selected were likely to be a subsection of the normal epithelium of the cervix, the os or the transformation zone. From direct observation, the Gabor segments were in approximately the same regions for both VIA and VILI for 130/134 of the images. The Gabor segmented enabled the automatic selection of a region of interest for further analysis with the color and Haralick's texture features.

Haralick's texture features. VIA positive images had significantly high contrast (p=0.03), not significantly different correlation, significantly lower energy (p=0.013) and significantly lower homogenity (p=0.02) compared to VIA negative images. This is expected since "contrast" corresponds to variations between pixels (0 for a constant image), correlation looks at a mutual relationship between pixels (range: −1 to 1, with Nan for a constant image), energy corresponds to uniformity, with higher values for similar pixels (0-1 with 1 for a constant image) and homogenity reflects closeness in distribution to the diagonal of GLCM elements (range: 0-1, with 1 for diagonal/constant image), which calculate how often a pair of pixels with specific values and spatial relationship occur in an image. VILI positive images had significantly higher contrast (p=0.003), insignificantly different correlation, significantly lower energy (p=0.024) and significantly lower homogeneity (0.015) compared to VILI negative images. FIG. 2 shows representative images for Haralick's texture features.

Color transforms features. Each image was transformed into 5 main color spaces and the central tendencies and Otsu threshold calculated. FIG. 2 shows representative color transforms for the VIA (YCbCr-Cb) and VILI (CIElab-b) images. As shown, lesion regions for VILI tended to have lower values than non-lesion regions in the b channel. In the Cb channel for VIA, lesion regions tended to have higher values than non-lesion regions. Different color channels showed distinct trends as well as redundancies. The optimal combination of features was later addressed using the sequential feature selection method. FIG. 2 illustrates endpoints for feature extraction methods used for VIA and VILI classification. From left, the figure shows original VIA negative and positive images, and VILI negative and positive images. This is followed by specular reflection attenuation results which demonstrate significantly reduced speckle and convincing infilling. Gabor segmentation selects a highly texturized region of the image for further processing. The area around the os is selected and for positive regions in particular, the area around the lesion. Haralick's texture output of the image is also shown with low homogeneity in lesion regions and high homogeneity in non-lesion regions.

Color transforms of the segments are also performed to take advantage in staining differences for negative and positive cervix images. Finally, for VILI images, approximate lesion size is determined.

Pseudo lesion size detection. Pseudo lesion size detection was performed on pre-processed VILI images since they enabled higher color-based contrast between lesion and non-lesion regions than VIA. We found that a threshold of 40 in the b channel of CIElab color space enabled adequate cutoff between the yellow and brown regions of the VILI images, the percentage of pixels above a threshold of 40 (which corresponds to all shades of yellow) was divided by the total cervical area to compute lesion size. The mean lesion size was found to be significantly higher ($p=0.0047$) in VILI negatives than in VILI positives as expected.

C. Feature Selection

Feature selection was performed to select a subset of features to prevent overfitting. Rather than use a simple filter method which selects features with the highest p-values, we used a wrapper forward sequential feature selection (FSFS) method which takes into consideration feature redundancies and interaction. The list of selected features and their p-values are in Table II.

FIG. 3 compares classifications scores from using top features by p-value (simple filter method) and by wrapper FSFS method. a) Box plots of classification scores for VIA algorithm using the features with the highest p-values, b) Box plots of classification scores for VIA algorithm using features selected with sequential feature sub-selection method, c) ROC curves comparing VIA results from features with simple filter method to FSFS method, d) Box plots of classification scores for VILI algorithm using the features with the highest p-values, e) Box plots of classification scores for VILI algorithm using features selected with sequential feature sub-selection method, f) ROC curves comparing VILI results from features with simple filter method to FSFS method. *=$p<0.05$, =$p<0.001$, *=$p<0.0001$, ****=$p<0.00001$.

D. SVM Classification

FIGS. 4a and 4b show scatterplots of classification scores for the parallel and serial combination methods. Classification scores are outputs from the SVM classifier indicating the probability/likelihood of an image belonging to either the negative or positive class. Scatterplots show similar expected trends for both methods. ROCs were generated to compare how the different algorithms (VIA, VILI parallel combined and ground truth for normal/benign vs. CIN+, normal/benign vs. low grade/CIN1 and normal/benign vs. high grade/CIN2+. Performance of three expert physicians (>15 years' of colposcopy experience per person) for the same data set are also indicated on the curve. The physician interpretations were collected retrospectively and were based on features from both VIA and VILI image interpretation. Hence physicians had the same information as the combined VIA and VILI algorithms. All physician performance points fall within the ROC curve for combined VIA and VILI algorithms, indicating superior algorithm performance, which is critical considering experts like the ones used in this study are not widely available and certainly lacking in low resource areas. Both combined algorithms outperformed the algorithms using the single contrasts but

TABLE II

Features and P-values from Simple Filter Method and Sequential Feature Sub-selection Method

| VIA | | | | VILI | | | |
|---|---|---|---|---|---|---|---|
| Features w/top p-values | | Sequential selected | | Features w/top p-values | | Sequential selected | |
| Feature | P-value | Feature | P-value | Feature | P-value | Feature | P-value |
| Correlation | 0.0009 | A mode | 0.07108 | CB median | 0.0001 | B mode | 0.0005 |
| Blue variance | 0.0016 | B mode | 0.2077 | CB mean | 0.0001 | Red variance | 0.5681 |
| L variance | 0.0065 | CR mode | 0.6073 | CB mode | 0.0001 | CB mean | 0.0001 |
| Y variance | 0.007 | Energy | 0.0009 | CB level | 0.000195 | CB level | 0.0002 |
| Grey variance | 0.007 | Correlation | 0.90849 | H mean | 0.00024 | Red mode | 0.17415 |
| Green variance | 0.0147 | CR level | 0.5717 | B mean | 0.00042 | V mode | 0.3329 |

FIG. 3 compares results of classification scores for VIA and VILI, achieved using features selected from the simple filter selection method and the forward sequential feature selection (FSFS). Results from VIA and VILI images show that features selected with the FSFS method shows expected trends in pre-cancer grades and significantly higher differences and AUC between normal/benign and CIN+ compared to intuitively selected features from the simple filter selection method.

achieved similar AUCs. Additionally, AUCs for VIA and VILI only AUCs were also similar.

FIG. 4 illustrates performance of different classification algorithms. a) Scatterplot for classification scores from parallel combined method, b) Scatterplot for classification scores from serial combined method, c) ROC curves for all algorithms for normal/benign vs CIN+, d) ROC curves for all algorithms for normal/benign vs low grade/CIN1, e) ROC curves for all algorithms for normal/benign vs CIN2+.

Performance of each expert physician reader (n=3) is also indicated for each graph. # of images refers to the number of images/image number.

Figure 5A:
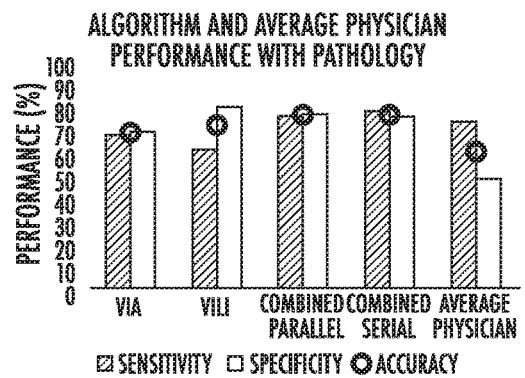
FIGS. 5A-C includes bar charts for classification performance between the algorithm, physicians, and pathology.
Figure 5B:
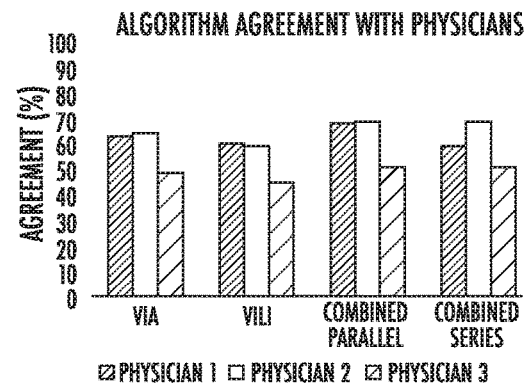
Figure 5C:
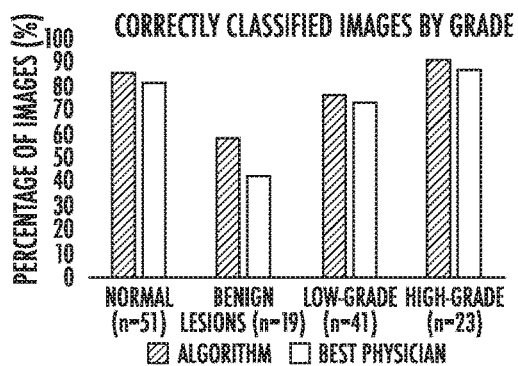
Figure 5D:
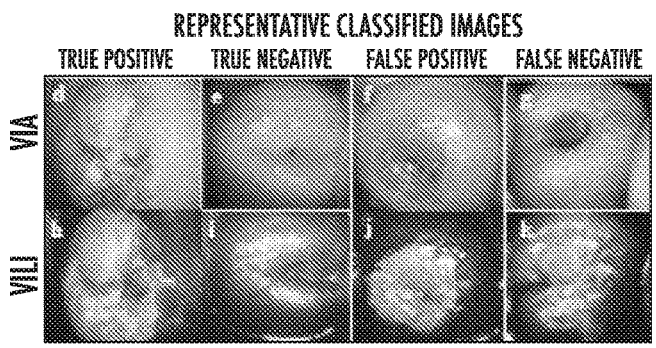
FIG. 5D illustrates representative VIA images and corresponding VILI images diagnosed by the algorithm.

FIG. 5 shows algorithm and each individual physician's sensitivities, specificities and accuracy as compared to pathology (FIGS. 5a and b).

Where sensitivity also known as the true positive rate measures the proportion of correctly identified positive, specificity also known as true negative rate measures the serially combined) performed compared to the pathology proportion of correctly identified negative cases and accuracy measures the overall proportion of correctly identified cases. Overall accuracy for all algorithms are higher than physician accuracies. Though physician's sensitives are on average on par with algorithms, algorithms achieve higher specificities. Combined algorithms achieved highest agreement with physicians, particularly with physicians who had higher performance with pathology. This is predictable since physicians also used both VIA and VILI images for prediction. FIG. 5c shows the percentage of correctly classified images by pre-cancer grade for one of the combined (serial) algorithms and the best physician. The algorithm outperforms the best physician across all cervix types but most notably for benign lesions which tend to be overcalled by physicians. FIGS. 5d-k shows representative VIA/VILI cervigrams of true positive, true negatives, false positives and false negative images classified by the serially combined algorithm. FIGS. 5d-g show VIA images with their corresponding VILI cervigrams in FIGS. 5h-k. True positive images showed acetowhitening and mosaicism in VIA image (FIG. 5d) and yellow staining in VILI image (FIG. 5h). True negatives showed little to no visible whitening or mosaicism in VIA positive image (FIG. 5e) and showed brown staining from iodine uptake in VILI image (FIG. 5i). False positive images classified as negative by pathology but positive by the algorithm were due to high texture in the VIA image (FIG. 5f) and the non-uptake of Lugol's iodine in the VILI image (FIG. 5j). The false negative showed no distinct acetowhitening in the VIA image (FIG. 5g) and very little area of Lugol's non-uptake in the VILI image (FIG. 5k). This may be a result of the limitation where biopsies are taken from the endocervical canal which is not typically visible in the image.

To conclude, these images as well as all the errors of the automatic algorithms "make sense" and are a result from non-trivial images (recall that we compared with pathology, which is data not available to the algorithm or to the clinician).

Processing Time Analysis

We ran 10 randomly selected images through the algorithm and measured the machine time taken for individual steps and the overall time. For each image preprocessing for specular reflection attenuation and Gabor segmentation took the most time, averaging 27.7 seconds and 21.6 seconds, respectively, while feature extraction and classification took less than a second. Overall time taken per image averaged 50.3 seconds, and was 2 minutes at most, demonstrating the feasibility for real time diagnosis of images (FIG. 6).

Figure 6:
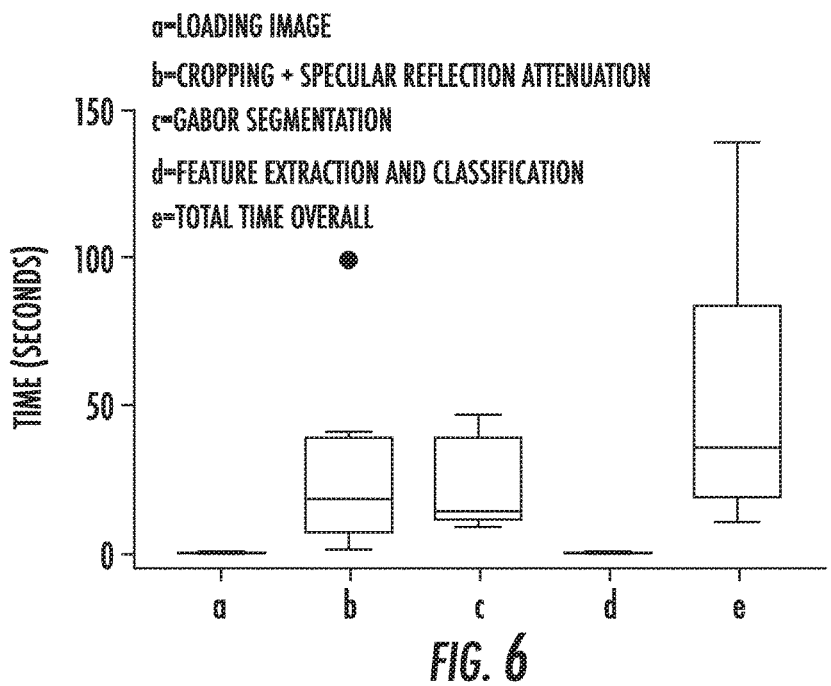
FIG. 6 includes box plots showing time taken (in seconds) to load, pre-process, process and classify a sample of the images (n=10) as positive or negative for pre-cancer.

FIG. 6 includes box plots showing time taken (in seconds) to load, pre-process, process and classify a sample of the images (n=10) as positive or negative for precancer. All but one of the images had a processing time of less than 2 minutes.

IV. Discussion

We introduced in this study algorithms (methods) to process and classify VIA and VILI cervigrams as negative or positive for cervical pre-cancer and to combine features from both contrasts to improve overall specificity while maintaining sensitivity.

Algorithms for the individual contrasts were developed to extract color and texture-, based features. A subset of the domain/expertise-motivated features was automatically selected and used to train a support vector machine to develop models for binary classification of cervigrams. The individual algorithms were combined both in parallel (both at the same time, simultaneously with SVM scores) and serially (VIA followed by VILI) to improve performance. Combined methods performed on par with each other, with the parallel method achieving a sensitivity, specificity, accuracy and AUC of 79.7%, 80.0%, 80.0%, and 0.86, respectively, and the serially combined algorithm achieving a sensitivity, specificity, accuracy, and AUC of 81.3%, 78.6%, 80.0%, and 0.86, respectively. This was higher than average expert physicians, who achieved a sensitivity, specificity and accuracy of 77%, 51%, and 63%, respectively. The algorithm more accurately classified negatives, benign conditions, low grades and high-grade conditions than the best performing physician.

This algorithm has been developed with images captured using the Pocket Colposcope, a low-cost, portable, digital colposcope. The labeled images used for this study were obtained retrospectively and physicians used both VIA and VILI data, hence we were not able to directly compare the individual algorithms for VIA and VILI. No previous algorithms for combining VIA and VILI classification have been developed to which we can compare our results. There was only one study we found that had proposed a method to combine VIA and VILI images for diagnoses. However, though preliminary representative images from color-based segmentation were shown, no quantitative performance of the VILI algorithm was provided to which we could compare our results. Additionally, there is no previous algorithm that uses VILI alone for cervical pre-cancer diagnosis. Several groups have proposed methods towards automatic VIA diagnosis which, include automated cervix segmentation, specular reflection removal, and cetowhitening detection using color-based and texture features. However, most of these are only semi-automated, requiring manual ROI selection and focusing on lesion detection within abnormal VIA images. Manually selected regions are then classified as a type of cervix tissue using various classifiers. Even though some groups have started working to enable full automation, the current methods cite device- and illumination-dependence, and image diversity being cited as a major challenge in analysis.

Physician performance in our study is on par to those from previous studies. A colposcopy study by Qureshi et al with 328 women found a sensitivity of 86.84% and a specificity of 48.93f %. A study in Tanzania by Ngoma et al of 10,367 women screened with VILI found a range of 79.8%-99.3% for sensitivity and 97.0%-97.6% for specificity. Sankaranarayanan et al performed a study with 4,444 women in Kerala, India, and found a range of 80.6%-92.0% for sensitivity and 83.6%-85.8% for specificity. Our physician performance ranged from 68.3-88.9% for sensitivity, 20.0-71.4% for specificity, and 52.6-70.1% for accuracy. It is interesting to note while the average sensitivity of physicians in this study was comparable to that reported in previous studies, the average specificity was lower. We speculate that this may be because physicians who participated in our study were viewing still images of VIA/VILI without any information on patient history or demographics compared to previous studies in which images were interpreted in real time. Additionally, the prevalence of disease is lower at the population level, which was the study population used in previous studies, compared to the diagnostic population (secondary screening), which was the study population investigated here. In the diagnostic population, there is a higher number of borderline benign conditions, which can be easily misinterpreted due to intrinsic properties of the contrast agents. Future studies may include testing the algorithm in a real time clinical setting and comparing its performance to pathology and expert physician interpretation in the field.

Overall, the algorithm for automated cervical cancer diagnosis performed significantly better than average diagnosis of expert physicians. The proposed algorithm requires very little training data, computational space and run time compared to other machine learning frameworks. Even though this algorithm is developed using images captured with the Pocket Colposcope, the method can potentially be applied to cervigrams from other colposcopes. Overall, this method has potential to enable colposcopy diagnosis in the absence of an expert physician or to complement his/her judgment. Combining VIA and VILI classification outperforms physicians, thus allowing accurate referral colposcopy to be more accessible at the primary care/community level setting. In some embodiments, the algorithms and classification models described herein can be implemented on mobile or portable devices such as laptops, smartphones, and tablet computers. Additionally in the processing steps, regularization can be applied in place of the feature selection step or in addition to the feature selection step, to prevent overfitting or underfitting. Finally even though we focus on support vector machine classifiers, other classifiers such as logistic regression and neural networks can be applied to this method. Using the hand-crafted features method described above, similar steps can be taken with other classifiers, by switching out the SVM for a different classifier. For deep learning methods such as neural networks, the idea would be to input a combination of VIA, VILI and GIVI images (pairwise or all three) into the model as inputs, or to input individual images and combine output classification scores for combined classification.

V. Extrapolating Methods Used to Additional Datasets Obtained for VIA Only, VILI Only, and VIA+VILI+GIVI Methods Images, pathology and physician labels were retrospectively obtained from a database of Pocket Colposcope images acquired in previous clinical studies. As part of the studies, blinded expert physicians provided a diagnosis for each patient from reviewing randomized digital cervigrams based on both VIA and VILI images.

Images were obtained from different clinical study sites: Duke University Medical Center, Durham, USA; La Liga Contra el Cancer, Lima, Peru; Kilimanjaro Christian Medical Center, Moshi, Tanzania; and University Teaching Hospital, Lusaka, Zambia. For each site, different contrasts were used. However as VIA is the base standard of care for visual inspection of the cervix, VIA images were obtained from all sites. We looked at different combinations: VIA only, VILI only, GIVI only, VIA+VILI, VIA+GIVI, and VIA+VILI+GIVI. Due to the differences in data collected we also compared combinations to their individual contrast to determine improvements, independent of differences in data sets. A table summarizing the different sites and images collected as well as their divisions as normal, low-grade or high grade is shown in Table III below.

TABLE III

Summary of different sites and images collected with subsets of normal, low-grade, or high-grade diagnosis indicated

| | VIA | | | VIA + VILI | | | VIA + GIVI | | | VIA + VILI + GIVI | | |
|---|---|---|---|---|---|---|---|---|---|---|---|---|
| | Normal | Low Grade | High Grade | Normal | Low Grade | High Grade | Normal | Low Grade | High Grade | Normal | Low Grade | High Grade |
| DUMC | 35 | 23 | 54 | 5 | 12 | 12 | 22 | 19 | 34 | 5 | 12 | 12 |
| LLCC | 51 | 41 | 23 | 51 | 41 | 23 | N/A | N/A | N/A | N/A | N/A | N/A |
| KCMC | 2 | 6 | 10 | 2 | 6 | 10 | 2 | 6 | 8 | 2 | 6 | 8 |
| UTH | 3 | 3 | 33 | N/A | N/A | N/A | 2 | 3 | 32 | N/A | N/A | N/A |
| Total | 91 | 73 | 120 | 58 | 59 | 45 | 26 | 28 | 74 | 7 | 18 | 20 |

To summarize clinical study procedures, patients undergoing colposcopy examination at clinical study sites were recruited. These studies were approved by Duke University Institutional Review Board (Pro00052865) and performed with approved protocol, informed consent process, and data storage system for each international clinical study site. For each patient, acetic acid was applied to the cervix. Visual inspection was performed via standard of care (inspection with the naked eye, with magnification, colposcopy or cervicography), followed by imaging with the Pocket Colposcope using white light illumination.

For sites which performed GIVI, white light illumination image capture was followed by green light illumination image capture to highlight vasculature features on the cervix. For sites which performed VILI, Lugol's iodine was then applied to the cervix and VILI features were observed per standard of care visual inspection methods, followed by the Pocket Colposcope. Images, patient demographics, and pathology results were collected and stored in a HIPAA compliant secured database, REDcap. No biopsies were taken for cervices, which appeared normal during visual inspection as per standard-of-care procedures. However, some biopsies of cervices which appeared abnormal by visual inspection were at times determined to be normal by pathology.

Based on feedback from previous study, for algorithm binary classification labels, normal and CIN1s were grouped under "normal/benign". This is because most CIN1 cases are non-malignant and regress on their own, while CIN2+ cases are typically treated. Images, pathology and physician labels were retrospectively obtained from a database of Pocket Colposcope images acquired in previous clinical studies. As part of the studies, blinded expert physicians provided a diagnosis for each patient from reviewing randomized digital cervigrams based on both VIA and VILI images.

Additional images obtained with the pocket colposcope from other clinical studies were obtained. Depending on standard of care processes for each clinical site, contrasts contained were either VIA only, VILI only, GIVI only, VIA and GIVI, VIA and VILI, or all three. Using the methods described in detail above, pre-processing was performed to crop the cervix to remove any clinically irrelevant information such as the vaginal walls and speculum and specular reflection attenuation was applied to reduce the specular reflection in each image. After pre-processing, images were passed through the Gabor segmentation algorithm to segment a region of interest within the cervix for further analysis. From this region of interest, Haralick's texture features of contrast, correlation, homogeneity and energy, as previously described were extracted. The region of interest was also transformed into different color channels of color spaces and summary statistics obtained. These features were passed through the forward sequential feature selection (FSFS) algorithm to select a subset of optimal features for each contrast. Feature subsets were used to train 3 and cross-validate (10-fold) different classifiers: Support vector machine used previously, K-nearest neighbor classifier (KNN) and a generalized linear regression classifier to compare results.

From previous studies with VIA and VILI images from LLCC, Peru, combination methods for parallel combination was found to be slightly better than serial combination. Additionally, parallel combination enables simpler, and less subjective combination for contrast combinations than serial method, hence parallel combination methods was used to combine VIA+VILI, VIA+GIVI and VIA+VILI+GIVI images. Results were compared for: VIA only, VILI only, GIVI only, VIA+VILI, VIA+GIVI, and VIA+VILI+GIVI.

Results

VIA Only

Figure 7:
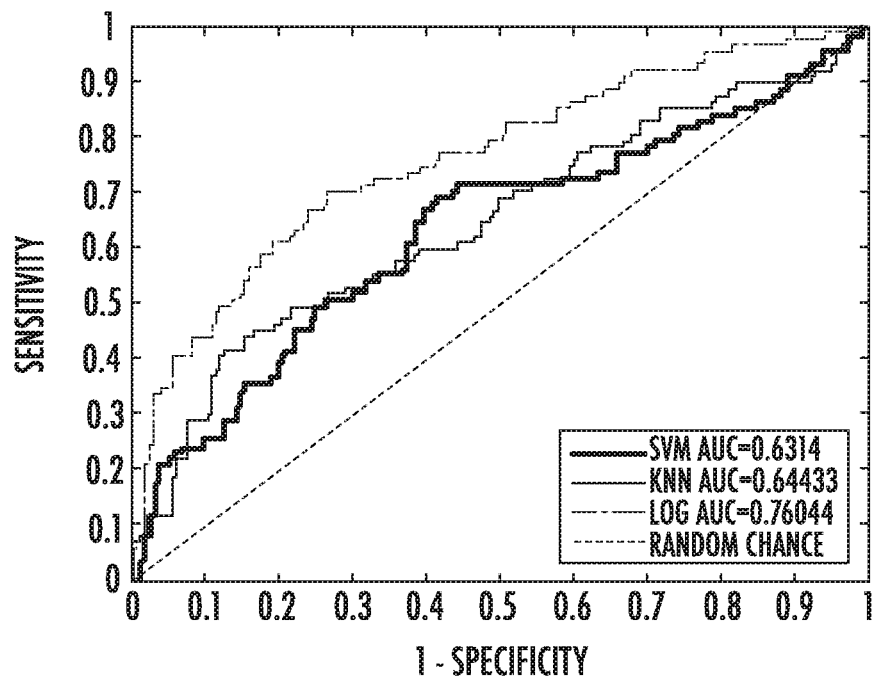
FIG. 7 is a graph showing results from algorithms using different classifiers for VIA images only.

VIA cervigrams were obtained from all study sites with 284 total images obtained. Of the 284 images, 91 were normal, 73 were CIN1 and 120 were CIN2+. Results are shown in FIG. 7 for 10-fold cross validation of selected features using SVM, KNN and Log classifiers. Of the three, the Log classifier performed best, obtaining an AUC of 0.76, this was followed by the SVM then KNN methods. Unlike the initial feasibility study with Peru data set, which was analyzed as normal vs CIN+, this data was analyzed as normal/CIN1 vs CIN+. Thus, different features were selected, and a different classifier model used. ROC curves for all individual classifiers as well as for combined classifiers are also shown. Results demonstrate a performance on par with initial algorithm using Peru data.

VIA and VILI

Figure 8:
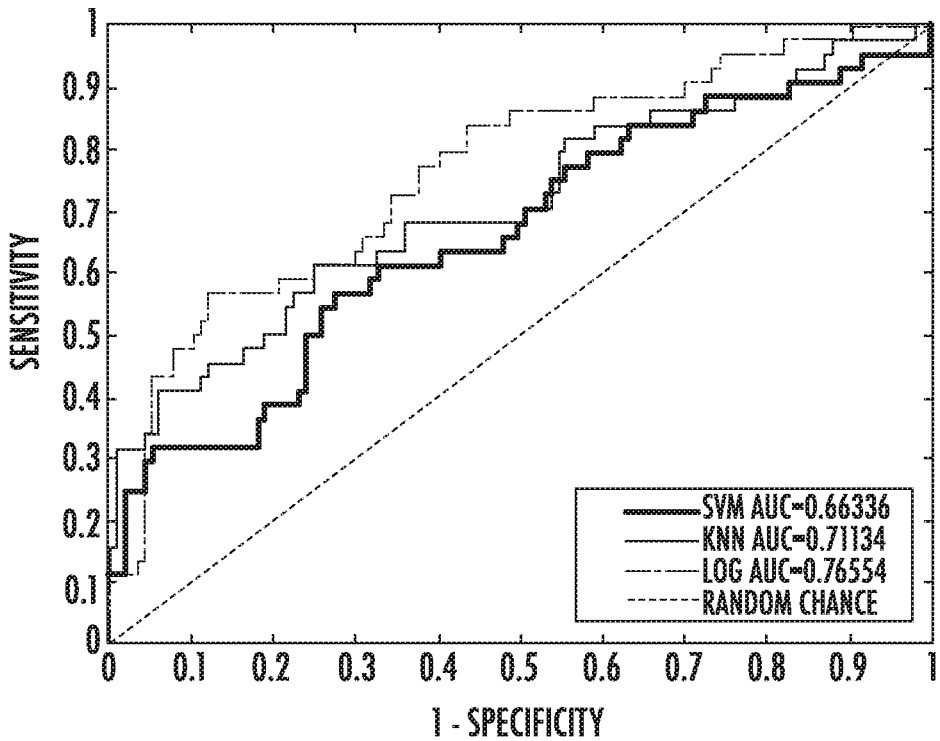
FIGS. 8-10 are graphs showing results from algorithms using different classifiers for VIA and VILI cervigram pairs.
Figure 9:
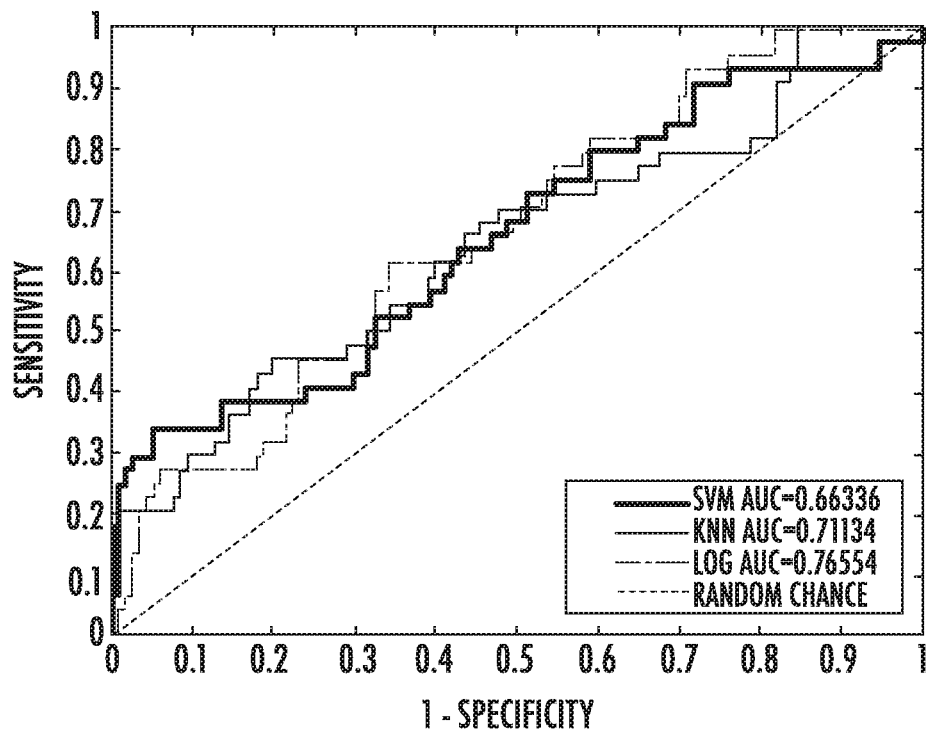
Figure 10:
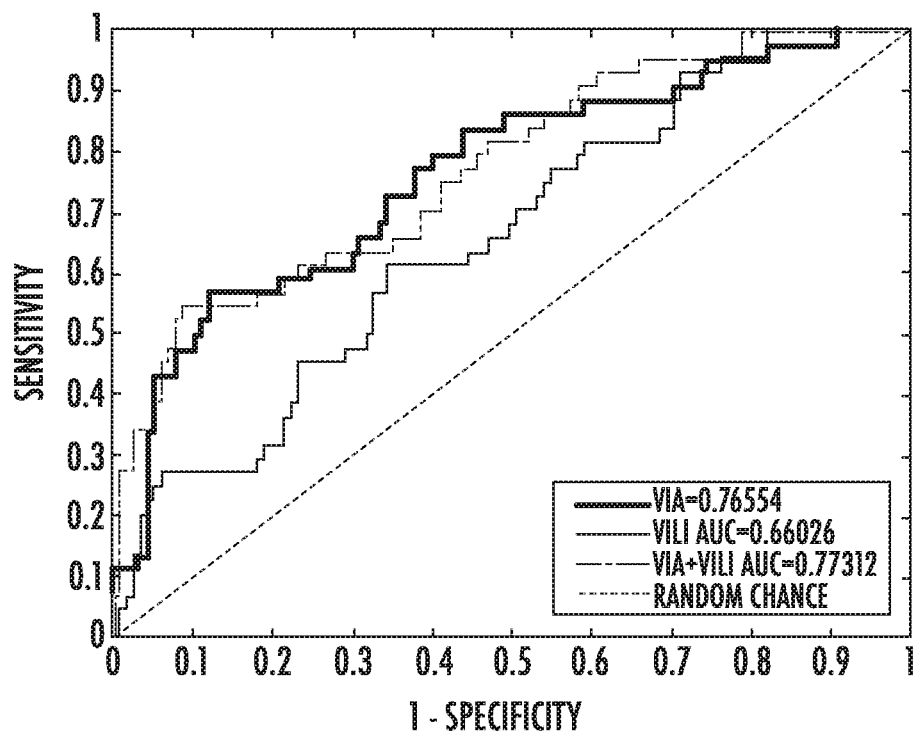

VIA and VILI Cervigram pairs were obtained from patients from LLCC, UTH, and a subset of DUMC patients. This yielded a total of 162 image pairs, of which 58 were normal, 59 were CIN1 and 45 were CIN2+. As per previous methods, normal/CIN1 were binned in the normal category for algorithm classification, while CIN2+ was binned in the abnormal category. Since data was heavily skewed within the binned normal category, a randomly selected subset of data (n=50) was selected from the Normal/CIN1 for training and cross validating the algorithm. Results are shown in FIGS. 8-10 for VIA only for this subset of data, VILI only and VIA+VILI combinations using the parallel combination methods. ROC curves for VIA only, VILI only and VIA+VILI are shown. Scatter plots for the best performing classifier, Log for VIA, VILI and VIA+VILI are also shown. Results demonstrate that combining VIA and VILI algorithms using the with 133 entire data set, outperforms physicians interpretation from initial study, and VIA is improved, though only marginally by addition of VILI contrast. Discrepancies in results between the two data sets may be from additional data set and from the classification of normal/CIN1 as abnormal and CIN2+.

VIA and GIVI

Figure 11:
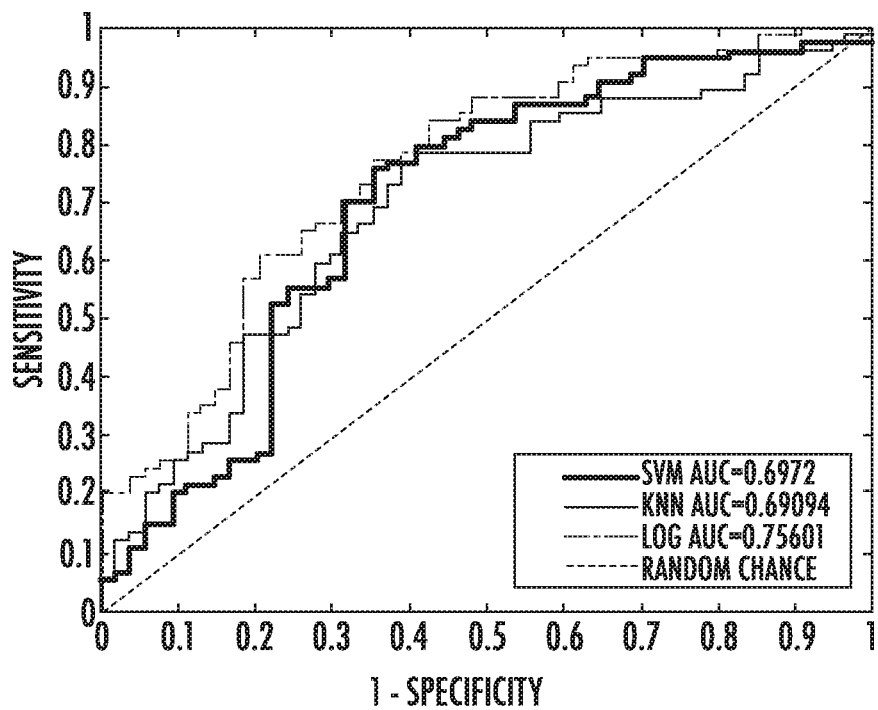
FIGS. 11-13 are graphs showing results from algorithms using different classifiers for VIA and GIVI cervigram pairs.
Figure 12:
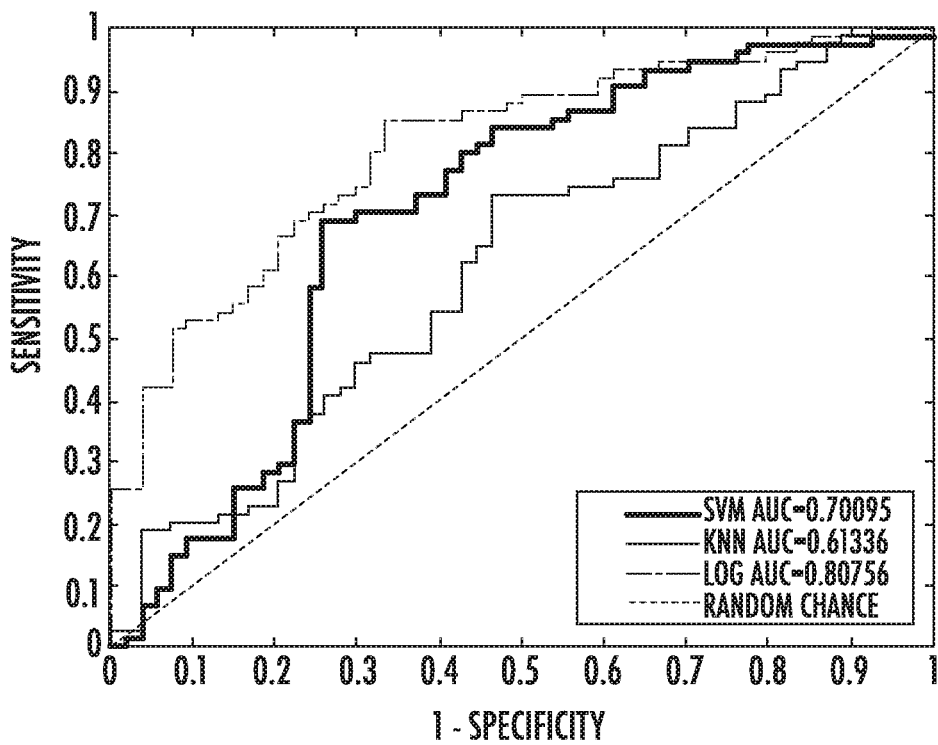
Figure 13:
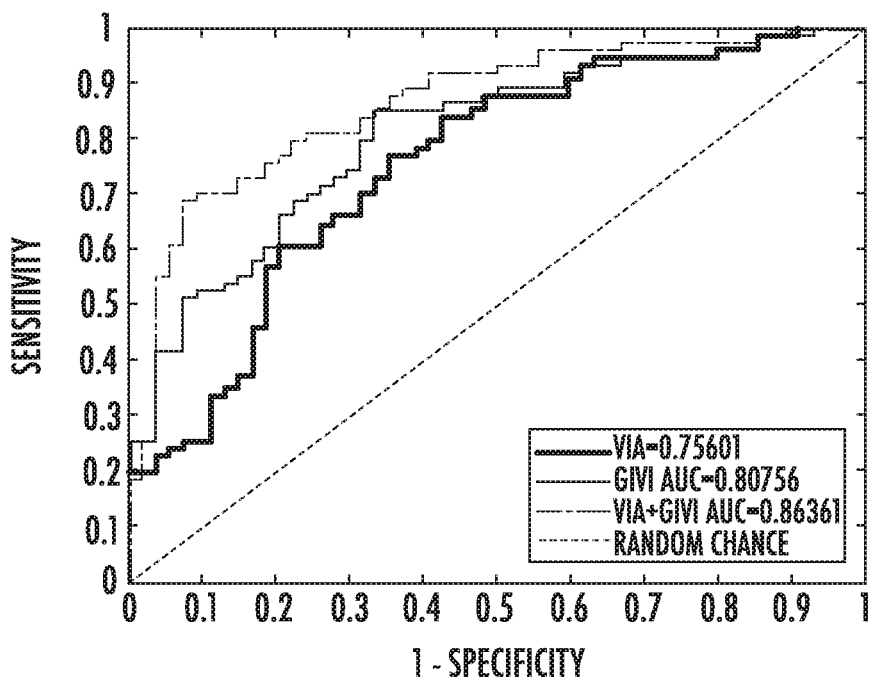

VIA and GIVI cervigram pairs were obtained from patients from KCMC, UTH and a subset of DUMC patients. This yielded a total of 128 image pairs with 26 normal, 28 low-grade and 74 high grades, with normal/CIN1 in normal category and CIN2+ in abnormal category. FIGS. 11-13 show results for VIA only, GIVI only for this particular data set and VIA+GIVI combination of the individual classification scores. ROC curves for VIA only, GIVI only and VIA+GIVI are shown. Results demonstrate that combining VIA and GIVI algorithms out performs VIA only or GIVI only.

VIA, VILI, and GIVI

Figure 14:
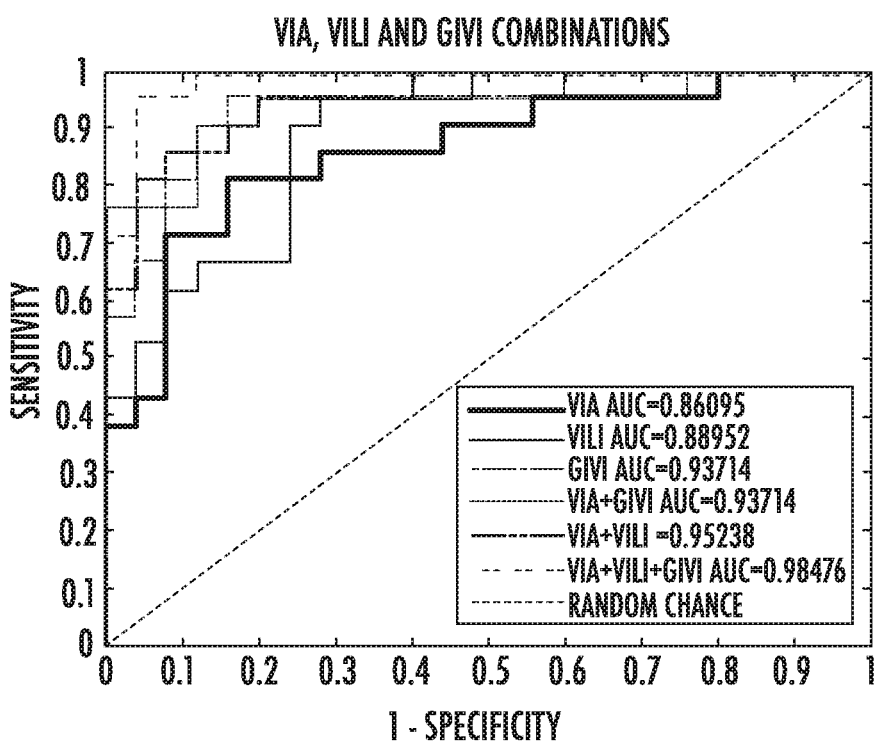
FIG. 14 is a graph showing results from algorithms using different classifiers for corresponding VIA, VILI, and GIVI cervigrams.

Of all the data collected, only a small subset of DUMC images and a subset of KCMC images had all three sources of contrast. This yielded a total of 45 image trios with 7 normal, 18 CIN1 and 20 CIN2+. FIG. 14 shows results for VIA, VILI, GIVI, VIA+VILI, VIA+GIVI and VIA+VILI+GIVI for this particular data set. Combinations of algorithms are done using the parallel combination method. A chart showing AUC scores for individual algorithms as well as all the different combinations are also shown. Log out performs both SVM and KNN in this case also. We also see that addition of an additional contrast improves over VIA only while, combining all three contrasts provides the best results. Since this is a small data set, results may be overly optimistic, seeing as the performance is higher than the algorithms performance on larger data sets. However, the trend in improvement with contrast addition is still relevant for VIA+VILI+GIVI sets.

Results

We developed algorithms to improve diagnostic accuracy for colposcopy images captured with the pocket colposcope and reduce inter-physician variability. The algorithms also promote task-shifting to community health workers since it reduces uncertainty with diagnostics and amount of training needed. For the algorithms we also demonstrate improvement in accuracy with additional sources of contrast. Initial proof-of-concept algorithms were developed on a data set from La Liga Contra el Cancer in Peru which had both VIA and VILI image pers. Image processing algorithms were developed to pre-process images, extract color and texture features, and classify images based on a selected subset of the features. Individual algorithms demonstrated performance on par with expert physicians reading of the same data set, while combined VIA and VILI algorithms significantly improved over the expert physicians. Based on these results algorithms were developed and tested on additional images reflecting additional sources of contrast. On a larger VIA data set algorithm performed on par with physician performance as demonstrated before. VIA+VILI and VIA+GIVI algorithms both demonstrated improvements over VIA only, while VIA+VILI+GIVI demonstrated the best performance of all of the algorithms.

The various operations and steps described herein may be carried out automatically and/or programmatically. The algorithms and classification models described herein were developed using MATLAB. However, other programming languages, such as C or Python, may be used. As used herein, the term "automatically" means that the operation is substantially, and may be entirely, carried out without human or manual control, direction and/or input, and can be programmatically directed or carried out. As used herein, the term "programmatically" refers to operations directed and/or primarily carried out electronically by computer program modules, code and/or instructions.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention. Therefore, it is to be understood that the foregoing is illustrative of the present invention and is not to be construed as limited to the specific embodiments disclosed, and that modifications to the disclosed embodiments, as well as other embodiments, are intended to be included within the scope of the invention.

What is claimed is:

1. A method for automated detection of cervical pre-cancer, the method comprising:
   providing at least one cervigram;
   pre-processing the at least one cervigram including automatically segmenting a region from the cervix for further analysis;
   extracting texture-based features from the segmented region of the at least one pre-processed cervigram; and
   classifying the at least one cervigram as negative or positive for cervical pre-cancer based on the extracted features.

2. The method of claim 1 wherein the pre-processing step comprises applying specular reflection attenuation to reduce specular reflection in the at least one cervigram.

3. The method of claim 1 wherein the pre-processing step comprises cropping the at least one cervigram to remove clinically insignificant features such as a speculum or vaginal walls, and wherein the cropping step optionally comprises automatically cropping the at least one cervigram.

4. The method of claim 1 wherein the automatically segmenting step is carried out using a Gabor filter, and wherein the segmented region optionally has the highest mean Gabor response.

5. The method of claim 1 wherein the extracting step comprises calculating Haralick's features including contrast, correlation, energy, and homogeneity for the segmented region.

6. The method of claim 1 wherein the extracting step comprises transforming the segmented region to different color spaces and, for each color channel of each color space, calculating central tendencies of mean, median, mode, and variance and Otsu threshold level.

7. The method of claim 1 wherein the at least one cervigram comprises a VILI image, and wherein the extracting step comprises determining a pseudo lesion size based on the percentage of pixels corresponding to the yellow staining from non-uptake of Lugol's iodine.

8. The method of claim 1 wherein the at least one cervigram comprises corresponding VIA and VILI images, and wherein the classifying step is carried out using a classification algorithm for VIA only images and a classification algorithm for VILI only images.

9. The method of claim 8 wherein the classifying step is carried out using a parallel-combined algorithm, and wherein prediction scores for classifying the VIA and VILI images with their respective algorithms are input as predictors to generate a classifier model for a combined classification.

10. The method of claim 8 wherein the classifying step is carried out using a serial-combined algorithm including:
    applying the classification algorithm for VIA only images to the VIA image to identify the VIA image as VIA negative or VIA positive;
    classifying the corresponding VIA and VILI images as negative if the VIA image is identified as VIA negative;
    if the VIA image is identified as VIA positive, applying the classification algorithm for VILI only images to the VILI image to identify the VILI image as VILI negative or VILI positive;
    classifying the corresponding VIA and VILI images as negative if the VILI image is identified as VILI negative; and
    classifying the corresponding VIA and VILI images as positive if the VILI image is identified as VILI positive.

11. The method of claim 1 wherein the at least one cervigram comprises corresponding VIA and GIVI images, and wherein the classifying step is carried out using a classification algorithm for VIA only images and a classification algorithm for GIVI only images.

12. The method of claim 1 wherein the at least one cervigram comprises corresponding VIA, VILI, and GIVI images, and wherein the classifying step is carried out using a classification algorithm for VIA only images, a classification algorithm for VILI only images, and a classification algorithm for GIVI only images.

13. A method for developing an algorithm for automated cervical cancer diagnosis, the method comprising:
    providing a plurality of cervigrams;
    pre-processing each cervigram including automatically segmenting a region from the cervix for further analysis;
    extracting texture-based features from the segmented region of each pre-processed cervigram; and
    establishing a classification model based on the extracted features for each cervigram,
    wherein the classification model is configured to classify additional cervigrams as negative or positive for cervical pre-cancer.

14. The method of claim 13 wherein the pre-processing step comprises applying specular reflection attenuation to reduce specular reflection in each cervigram.

15. The method of claim 13 wherein the pre-processing step comprises cropping at least some of the plurality of cervigrams to remove clinically insignificant features such as a speculum or vaginal walls, and wherein the cropping step optionally comprises automatically cropping the at least some of the plurality of cervigrams.

16. The method of claim 13 wherein the automatically segmenting step is carried out using a Gabor filter, and wherein the segmented region optionally has the highest mean Gabor response.

17. The method of claim 13 wherein the extracting step comprises calculating Haralick's features including contrast, correlation, energy, and homogeneity for the segmented region.

18. The method of claim 13 wherein the extracting step comprises transforming the segmented region to different color spaces and, for each color channel of each color space, calculating central tendencies of mean, median, mode, and variance and Otsu threshold level.

19. The method of claim 13 wherein at least one of the plurality of cervigrams comprises a VILI image, and wherein the extracting step comprises determining a pseudo lesion size based on the percentage of pixels corresponding to the yellow staining from non-uptake of Lugol's iodine.

20. The method of claim 13 wherein the establishing step comprises selecting an optimal subset of the extracted features for each cervigram for optimal training and to prevent over fitting of the classification model, and wherein the selecting step is optionally carried out using forward sequential feature selection that considers redundancy of feature selection as well as feature interaction.

21. The method of claim 13 wherein the establishing step comprises regularization of the extracted features to prevent overfitting or underfitting.

22. The method of claim 13 wherein the plurality of cervigrams comprise corresponding VIA and VILI images, and wherein the establishing step is carried out using a classification algorithm for VIA only images and a classification algorithm for VILI only images.

23. The method of claim 22 wherein the establishing step is carried out using a parallel-combined algorithm, and wherein prediction scores for classifying the VIA and VILI images with their respective algorithms are input as predictors to generate the classification model for a combined classification.

24. The method of claim 22 wherein the establishing step is carried out using a serial-combined algorithm including:
   applying the classification algorithm for VIA only images to the VIA image to identify the VIA image as VIA negative or VIA positive;
   classifying the corresponding VIA and VILI images as negative if the VIA image is identified as VIA negative;
   if the VIA image is identified as VIA positive, applying the classification algorithm for VILI only images to the VILI image to identify the VILI image as VILI negative or VILI positive;
   classifying the corresponding VIA and VILI images as negative if the VILI image is identified as VILI negative; and
   classifying the corresponding VIA and VILI images as positive if the VILI image is identified as VILI positive.

25. The method of claim 13 wherein the plurality of cervigrams comprise corresponding VIA and GIVI images, and wherein the establishing step is carried out using a classification algorithm for VIA only images and a classification algorithm for GIVI only images.

26. The method of claim 25 wherein the establishing step is carried out using a parallel-combined algorithm, and wherein prediction scores for classifying the VIA and GIVI images with their respective algorithms are input as predictors to generate the classification model for a combined classification.

27. The method of claim 25 wherein the establishing step is carried out using a serial-combined algorithm including:
   applying the classification algorithm for VIA only images to the VIA image to identify the VIA image as VIA negative or VIA positive;
   classifying the corresponding VIA and GIVI images as negative if the VIA image is identified as VIA negative;
   if the VIA image is identified as VIA positive, applying the classification algorithm for GIVI only images to the GIVI image to identify the GIVI image as GIVI negative or GIVI positive;
   classifying the corresponding VIA and GIVI images as negative if the GIVI image is identified as GIVI negative; and
   classifying the corresponding VIA and GIVI images as positive if the GIVI image is identified as GIVI positive.

28. The method of claim 13 wherein the plurality of cervigrams comprise corresponding VIA, VILI, and GIVI images, and wherein the establishing step is carried out using a classification algorithm for VIA only images, a classification algorithm for VILI only images, and a classification algorithm for GIVI only images, wherein the establishing step is optionally carried out using a parallel-combined algorithm, and wherein prediction scores for classifying the VIA, VILI, and GIVI images with their respective algorithms are optionally input as predictors to generate the classification model for a combined classification.

29. The method of claim 13 wherein the establishing step is carried out using a support vector machine classifier, a logistic regression classifier, or a neural network classifier.

30. A computer program product for automated detection of cervical pre-cancer, the computer program product comprising a non-transitory computer readable storage medium having encoded thereon instructions that, when executed on a processor, cause the processor to perform the method of claim 1.

* * * * *

UNITED STATES PATENT AND TRADEMARK OFFICE
CERTIFICATE OF CORRECTION

| | | |
|---|---|---|
| PATENT NO. | : 12,073,559 B2 | Page 1 of 1 |
| APPLICATION NO. | : 17/282093 | |
| DATED | : August 27, 2024 | |
| INVENTOR(S) | : Asiedu et al. | |

It is certified that error appears in the above-identified patent and that said Letters Patent is hereby corrected as shown below:

On the Title Page

(60) Related U.S. Application Data: Please insert the following: --Provisional application No. 62/741,342, filed Oct. 4, 2018.--

In the Specification

Column 9, Line 45: Please correct "Peril" to read --Perú--

Signed and Sealed this
Seventeenth Day of December, 2024

Derrick Brent
*Acting Director of the United States Patent and Trademark Office*